(12) United States Patent
Shak et al.

(10) Patent No.: US 11,551,782 B2
(45) Date of Patent: *Jan. 10, 2023

(54) GENE EXPRESSION PROFILE ALGORITHM FOR CALCULATING A RECURRENCE SCORE FOR A PATIENT WITH KIDNEY CANCER

(71) Applicant: Genomic Health, Inc., Redwood City, CA (US)

(72) Inventors: Steven Shak, Hillsborough, CA (US); George Andrew Watson, Los Altos, CA (US); Michael R. Crager, Menlo Park, CA (US); Tara Maddala, Sunnyvale, CA (US); Margarita Lopatin, Palo Alto, CA (US); Audrey Goddard, San Francisco, CA (US); Dejan Knezevic, Palo Alto, CA (US); Christer Svedman, Stockholm (SE)

(73) Assignee: Genomic Health, Inc., Redwood City, CA (US)

( * ) Notice: Subject to any disclaimer, the term of this patent is extended or adjusted under 35 U.S.C. 154(b) by 248 days.

This patent is subject to a terminal disclaimer.

(21) Appl. No.: 17/086,850

(22) Filed: Nov. 2, 2020

(65) Prior Publication Data

US 2021/0151122 A1 May 20, 2021
US 2022/0044760 A9 Feb. 10, 2022

Related U.S. Application Data

(63) Continuation of application No. 16/199,707, filed on Nov. 26, 2018, now abandoned, which is a
(Continued)

(51) Int. Cl.
*C12Q 1/68* (2018.01)
*G16B 20/20* (2019.01)
(Continued)

(52) U.S. Cl.
CPC .......... *G16B 20/20* (2019.02); *C12Q 1/6886* (2013.01); *G16B 20/00* (2019.02); *G16C 99/00* (2019.02);
(Continued)

(58) Field of Classification Search
CPC ....................................................... C12Q 1/68
(Continued)

(56) References Cited

U.S. PATENT DOCUMENTS 7,135,314 B1 11/2006 Leung et al.
7,611,839 B2 11/2009 Twine et al.
(Continued)

FOREIGN PATENT DOCUMENTS

CA 2531091 A1 1/2005
CA 2530738 A1 5/2005
(Continued)

OTHER PUBLICATIONS

Affymetrix. Information retrieved on Jan. 8, 2019 from the internet: https://www.affymetrix.com/analysis/netaffx/showresults.affx# (2019).
(Continued)

*Primary Examiner* — Aaron A Priest
(74) *Attorney, Agent, or Firm* — McNeill Baur PLLC

(57) ABSTRACT

The present invention provides algorithm-based molecular assays that involve measurement of expression levels of genes from a biological sample obtained from a kidney cancer patient. The present invention also provides methods of obtaining a quantitative score for a patient with kidney cancer based on measurement of expression levels of genes from a biological sample obtained from a kidney cancer patient. The genes may be grouped into functional gene subsets for calculating the quantitative score and the gene subsets may be weighted according to their contribution to cancer recurrence.

19 Claims, 2 Drawing Sheets

A. Predictiveness curves for patients with stage 1 ccRCC

B. Predictiveness curves for patients with Stage 2 and Stage 3 ccRCC

Related U.S. Application Data continuation of application No. 14/779,428, filed as application No. PCT/US2014/040003 on May 29, 2014, now Pat. No. 10,181,008.

(60) Provisional application No. 61/829,100, filed on May 30, 2013.

(51) Int. Cl.
| | |
|---|---|
| *G16B 20/00* | (2019.01) |
| *G16C 99/00* | (2019.01) |
| *C12Q 1/6886* | (2018.01) |
| *G16H 50/30* | (2018.01) |
| *G16Z 99/00* | (2019.01) |

(52) U.S. Cl.
CPC ............ *G16H 50/30* (2018.01); *G16Z 99/00* (2019.02); *C12Q 2600/118* (2013.01); *C12Q 2600/158* (2013.01)

(58) Field of Classification Search
USPC ........................................................ 435/6.1
See application file for complete search history.

(56) References Cited

U.S. PATENT DOCUMENTS

| | | |
|---|---|---|
| 2002/0173461 A1 | 11/2002 | Pennica et al. |
| 2003/0109434 A1 | 6/2003 | Algate et al. |
| 2003/0180770 A1 | 9/2003 | Damokosh et al. |
| 2003/0022437 A1 | 12/2003 | Dai et al. |
| 2004/0088746 A1 | 5/2004 | Grimm et al. |
| 2004/0110197 A1 | 6/2004 | Skinner et al. |
| 2004/0110221 A1 | 6/2004 | Twine et al. |
| 2005/0002904 A1 | 1/2005 | Wary et al. |
| 2005/0048542 A1 | 3/2005 | Baker et al. |
| 2006/0088823 A1 | 4/2006 | Haab et al. |
| 2006/0183120 A1 | 8/2006 | Teh et al. |
| 2006/0281122 A1 | 12/2006 | Bryant et al. |
| 2007/0037186 A1 | 2/2007 | Jiang et al. |
| 2007/0099209 A1 | 5/2007 | Clarke et al. |
| 2007/0105133 A1 | 5/2007 | Clarke et al. |
| 2007/0224596 A1 | 9/2007 | Nacht et al. |
| 2008/0032299 A1 | 2/2008 | Burczynski et al. |
| 2008/0064055 A1 | 3/2008 | Bryant et al. |
| 2008/0119367 A1 | 5/2008 | Vasmalzis et al. |
| 2008/0182255 A1 | 7/2008 | Baker et al. |
| 2008/0242606 A1 | 10/2008 | Jiang |
| 2008/0286273 A1 | 11/2008 | Starmans et al. |
| 2009/0023149 A1 | 1/2009 | Knudsen et al. |
| 2009/0035312 A1 | 2/2009 | Griffioen et al. |
| 2009/0186924 A1 | 7/2009 | Billen et al. |
| 2009/0258002 A1 | 10/2009 | Barrett |
| 2009/0280490 A1 | 11/2009 | Baker et al. |
| 2010/0093768 A1 | 4/2010 | Nelson et al. |
| 2010/0152055 A1 | 6/2010 | Kozono et al. |
| 2011/0123990 A1 | 5/2011 | Baker et al. |
| 2011/0129833 A1 | 6/2011 | Baker et al. |
| 2011/0171633 A1* | 7/2011 | Cowens ................. G16B 99/00 435/6.1 |
| 2012/0142553 A1 | 6/2012 | Smit et al. |

FOREIGN PATENT DOCUMENTS

| | | |
|---|---|---|
| CA | 2621932 A1 | 3/2007 |
| CA | 2631236 A1 | 6/2007 |
| CA | 2633593 A1 | 10/2007 |
| JP | 2005211023 | 8/2005 |
| JP | 2008529554 A | 8/2008 |
| JP | 2009515148 A | 4/2009 |
| WO | 02079411 A2 | 10/2002 |
| WO | 2004048933 A2 | 6/2004 |
| WO | 2004097052 A2 | 11/2004 |
| WO | 2005117943 A2 | 12/2005 |
| WO | 2006089185 A2 | 8/2006 |
| WO | 2006124022 A2 | 11/2006 |
| WO | 2006124836 A1 | 11/2006 |
| WO | 2007026896 A1 | 3/2007 |
| WO | 2007045996 A1 | 4/2007 |
| WO | 2007072225 A2 | 6/2007 |
| WO | 2008021115 A2 | 2/2008 |
| WO | 2008138579 A1 | 11/2008 |
| WO | 2009105640 A1 | 8/2009 |
| WO | 2010056374 A2 | 5/2010 |
| WO | 2011085263 A2 | 7/2011 |
| WO | 2012174282 A2 | 12/2012 |
| WO | 2013028807 A2 | 2/2013 |

OTHER PUBLICATIONS

Anders M., et al., "Microarray Meta-analysis Defines Global Angiogenesis-related Gene Expression Signatures in Human Carcinomas," Molecular Carcinogenesis, 2011.

Annual Meeting of the Japanese Cancer Association, 2006, vol. 65, pp. 367, p. 888.

Baldewijns et al., "High-grade clear cell renal cell carcinoma has a higher angiogenic activity than low-grade renal cell carcinoma based on histomorphological quantification and qRT-PCR mRNA expression profile," British Journal of Cancer 96:1888-1895 (2007).

Chan E., et al., "Integrating Transcriptomics and Proteomics," G & P Magazine, 2006, vol. 6 (3), pp. 20-26.

De Kok J.B., et al., "Normalization of Gene Expression Measurements in Tumor Tissues: Comparison of 13 Endogenous Control Genes," Laboratory Investigation, 2005, vol. 85 (1 ), pp. 154-159.

Dekel et al., "Multiple Imprinted and Sternness Genes Provide a Link between Normal and Tumor Progenitor Cells of the Developing Human Kidney," Cancer Res. 66(12):6040-6049 (2006).

Extended European Search Report dated Aug. 10, 2017, European Patent Application No. 17153152.8.

Extended European Search Report dated Dec. 23, 2016, for European Patent Application No. 14804772.3.

Extended European Search Report dated Jul. 28, 2016, for European Application No. 15203193.6, 12 pages.

Extended European Search Report issued in European Application No. 19173150.4, dated Aug. 2, 2019, 9 pages.

GenBank: AB385541.1, Oct. 3, 2008, 2 pages.

GenBank: AF043329.1, Jan. 5, 1999, 2 pages.

Haller et al., "Equivalence Test in Quantitative Reverse Transcription Polymerase Chain Reaction: Confirmation of Reference Genes Suitable for Normalization", Analytical Biochemistry, 2004, vol. 335, No. 1, pp. 1-9.

Hata et al., "Expression of Th2-skewed Pathology Mediators in Monocyte-Derived Type 2 Dendritic Cells (DC2)," Immunology Letters, vol. 126, 2009, pp. 29-36.

Hoshikawa Y., et al., "Hypoxia Induces Different Genes in the Lungs of Rats Compared with Mice," Physiological Genomics, 2003, vol. 12 (3), pp. 209-219.

International Search Report and Written Opinion for Application No. PCT/US2011/020596, dated Nov. 25, 2011, 10 pages.

International Search Report and Written Opinion dated Oct. 10, 2014 for International Patent Application No. PCT/US2014/040003.

Jansson et al., "Nitric Oxide Synthase Activity in Human Renal Cell Carcinoma," J. Urol. 160(2):556-560, 1998.

Jones et al., "Gene Signatures of Progression and Metastasis in Renal Cell Cancer," Clin. Cancer Res. 11 (16):5730-5739 (2005).

Jung et al., "In search of suitable reference genes for gene expression studies of human renal cell carcinoma by real-time PCR," BMC Molecular Biology 8:47 (2007).

Kosari et al., "Clear Cell Renal Cell Carcinoma: Gene Expression Analyses Identify a Potential Signature for Tumor Aggressiveness," Clin. Cancer Res. 11(14):5128-5139 (2005).

Lenburg et al., "Previously Unidentified Changes in Renal Cell Carcinoma Gene Expression Identified by Parametric Analysis of Microarray Data", BMC Cancer, vol. 3:31, 2003, 19 pp.

Li et al., "Rapid and Sensitive Detection of Messenger RNA Expression for Molecular Differential Diagnosis of Renal Cell Carcinoma," Clinical Cancer Research 9:6441-6446 (2003).

(56) References Cited

OTHER PUBLICATIONS

Maeurer et al., "Host immune response in renal cell cancer: Interleukin-4 (IL-4) and IL-10 mRNA are frequently detected in freshly collected tumor-infiltrating lymphocytes," Cancer Immunol. Immunother. 41:111-121 (1995).
NCBI Reference Sequence NM_003713.3, Oct. 22, 2008, 4 pages.
Osunkoya et al., "Diagnostic biomarkers for renal cell carcinoma: selection using novel bioinformatics systems for microarray data analysis," Human Pathology 40:1671-1678 (2009).
Partial European Search Report dated Apr. 11, 2016, for European Application No. 15203193.6, 7 pages.
Partial European Search Report dated May 8, 2017, European Patent Application No. 17153152.8.
Rini et al., "4501: Identification of prognostic genomic markers in patients with localized clear cell renal cell carcinoma (ccRCC)," J. Clin. Onocol. 28(15):4501, Suppl., 2010.
Rini et al., "A 16-gene assay to predict recurrence after surgery in localised renal cell carcinoma: development and validation studies," Lancet Oncol. 16:676-685 (2015).
Sanjmyatav et al., "A Specific Gene Expression Signature Characterizes Metastatic Potential in Clear Cell Renal Cell Carcinoma", Journal of Urology, vol. 186, No. 1, 2011, pp. 289-294.
Schuetz, et al., J. Mol. Diagn., 2005, vol. 7, No. 2, pp. 206-218.
Search Report and Written Opinion for Singapore Patent Application No. 201204514-2 dated Jul. 29, 2013.
Sengupta S., et al., "Histologic Coagulative Tumor Necrosis As a Prognostic Indicator of Renal Cell Carcinoma Aggressiveness," Cancer, 2005, vol. 104 (3), pp. 511-520.
Supplementary Data for Yang et al., "A Molecular Classification of Papillary Renal Cell Carcinoma", Cancer Research, vol. 65:13, 2005, pp. 5628-5637, 1 pg.
Takahashi M., et al., "Gene Expression Profiling of Clear Cell Renal Cell Carcinoma: Gene Identification and Prognostic Classification," Proceedings of the National Academy of Sciences, 2001, vol. 98 (17), pp. 9754-9759.
Tan X., et al., "Global Analysis of Metastasis-associated Gene Expression in Primary Cultures from Clinical Specimens of Clear-cell Renal-cell Carcinoma," International Journal of Cancer, 2008, vol. 123 (5), pp. 1080-1088.
Tang et al., "MYC pathway is activated in clear cell renal cell carcinoma and essential for proliferation of clear cell renal cell carcinoma cells," Cancer Letters, 273(1):35-43, 2009.
The Human Protein Atlas, retrieved on Jun. 27, 2018, from the internet: https://www.proteinatlas.org/ENSG00000113368-LMNB1/tissue, 2018, 3 pp.
Tomsig, et al., "Lipid Phosphate Phosphohydrolase Type 1 (LPP1) Degrades Extracellular Lysophasphatidic Acid in Vivo", Biochem J., vol. 419, 2009, pp. 611-618.
Unwin et al. "Proteomic changes in renal cancer and co-ordinate demonstration of both the glycolytic and mitochondrial aspects of the Warburg effect". Proteomics, 2003, vol. 3, pp. 1620-1632.
Vasselli et al., "Predicting survival in patients with metastatic kidney cancer by gene-expression profiling in the primarytumor," PNAS 100(12):6958-6963 (2003).
Whitehead A., et al., "Variation in Tissue-specific Gene Expression Among Natural Populations," Genome Biology, 2005, vol. 6 (2), R13.
Yang H., et al., "Caffeine Suppresses Metastasis in a Transgenic Mouse Model: A Prototype Molecule for Prophylaxis of Metastasis," Clinical and Experimental Metastasis, 2004, vol. 21(8), pp. 719-735.
Yang, et al., "A Molecular Classification of Papillary Renal Cell Carcinoma", Cancer Research, 2005, vol. 65, pp. 5628-5637.
Yao M., et al., "A Three-gene Expression Signature Model to Predict Clinical Outcome of Clear Cell Renal Carcinoma," International Journal of Cancer, 2008, vol. 123 (5), pp. 1126-1132.
Zhao H., et al., "Gene Expression Profiling Predicts Survival in Conventional Renal Cell Carcinoma," PLOS Medicine, 2006, vol. No. 3 (1), pp. 1-13.
Extended European Search Report issued in European Application No. 20210111.9, dated Sep. 16, 2021, 17 pages.
Kondo et al., High Expression of Chemokine Gene as a Favorable Prognostic Factor in Renal Cell Carcinoma, J. Urology 171(6):2171-2175 (2004).
Lane et al., "Differential Expression in Clear Cell Renal Cell Carcinoma Identified by Gene Expression Profiling", J. Urology 181(2):849-860 (2009).
Nogueira et al., "Molecular markers for predicting prognosis of renal cell carcinoma", Urologic Oncology 26 (2): 113-124 (2007).

* cited by examiner

A. Predictiveness curves for patients with stage 1 ccRCC
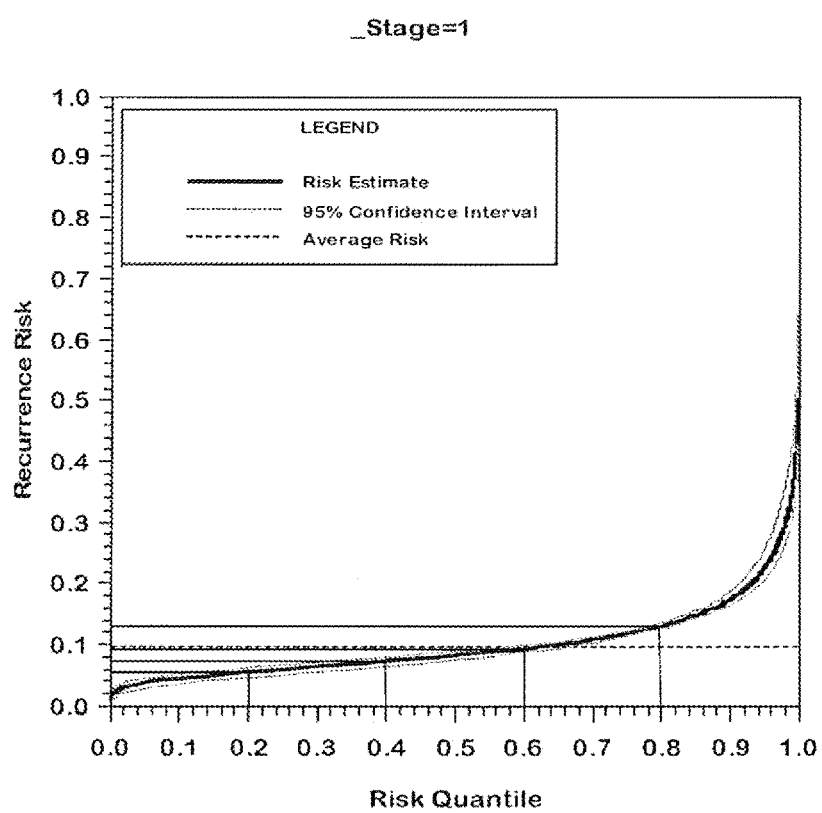

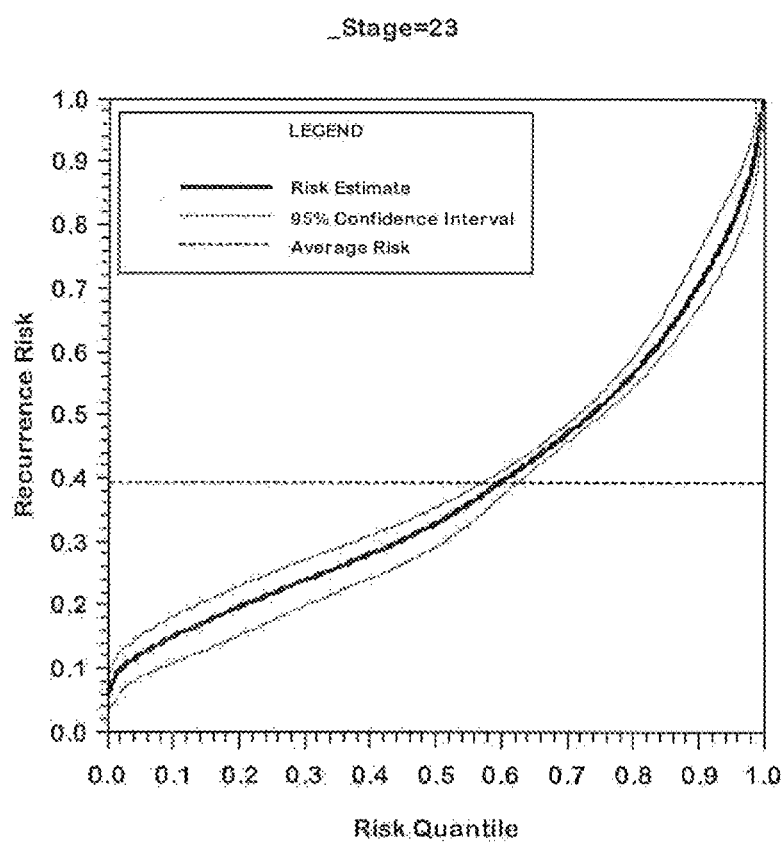
B. Predictiveness curves for patients with Stage 2 and Stage 3 ccRCC

… (1) …

GENE EXPRESSION PROFILE ALGORITHM FOR CALCULATING A RECURRENCE SCORE FOR A PATIENT WITH KIDNEY CANCER

CROSS REFERENCE TO RELATED APPLICATIONS

This application is a continuation of U.S. application Ser. No. 16/199,707, filed Nov. 26, 2018, which is a continuation of U.S. application Ser. No. 14/779,428, filed Sep. 23, 2015, which is a national phase entry pursuant to 35 U.S.C. § 371 of International Application No. PCT/US2014/040003, filed May 29, 2014, which claims the benefit of priority of U.S. Provisional Application No. 61/829,100, filed May 30, 2013, each of which is incorporated by reference herein in its entirety for any purpose.

TECHNICAL FIELD

The present disclosure relates to molecular diagnostic assays that provide information concerning gene expression profiles to determine prognostic information for cancer patients. Specifically, the present disclosure provides an algorithm comprising genes, or co-expressed genes, the expression levels of which may be used to determine the likelihood that a kidney cancer patient will experience a positive or a negative clinical outcome. The present disclosure provides gene expression information useful for calculating a recurrence score for a patient with kidney cancer.

INTRODUCTION

The American Cancer Society's estimates that in 2013 there will be about 65,150 new cases of kidney cancer and about 13,680 deaths from kidney cancer in the United States. (American Cancer Society, Kidney Cancer (Adult) Renal Cell Carcinoma Overview, available online at http://www.cancer.org/acs/groups/cid/documents/webcontent/003052-pdf.pdf). Renal cell carcinoma (RCC), also called renal adenocarcinoma or hypernephroma, is the most common type of kidney cancer, accounting for more than 9 out of 10 cases of kidney cancer, and it accounts for approximately 2-3% of all malignancies. (Id.; National Comprehensive Cancer Network Guidelines (NCCN) Clinical Practice Guidelines in Oncology, Kidney Cancer, Version 1.2013.) For unknown reasons, the rate of RCC has increased by 2% per year for the past 65 years. (NCCN Clinical Practice Guidelines in Oncology, Kidney Cancer.)

There are multiple subtypes of RCC, including clear cell renal cell carcinoma, papillary renal cell carcinoma, chromophobe renal cell carcinoma, collecting duct renal cell carcinoma, and unclassified renal cell carcinoma. Clear cell renal cell carcinoma (ccRCC) is the most common subtype of renal cell carcinoma, with about 7 out of 10 patients with RCC having ccRCC. (American Cancer Society, Kidney Cancer (Adult) Renal Cell Carcinoma Overview)

Evaluation and staging of RCC includes visualization via imaging methods, such as computed tomographic (CT) scan, ultrasound, or magnetic resonance imaging (MRI), and physical and laboratory evaluations. Needle-biopsy may be performed to diagnose RCC and guide surveillance of disease. Physicians classify tumors based on clinical and pathological features, such as tumor stage, regional lymph node status, tumor size, nuclear grade, and histologic necrosis. Such designations can be subjective, and there is a lack of concordance among pathology laboratories in making such determination (Al-Ayanti M et al. (2003) Arch Pathol Lab Med 127, 593-596), highlighting the need for more objective designations.

Treatment of RCC varies depending on the stage of the cancer, the patient's overall health, the likely side effects of treatment, the chances of curing the disease, the chances of improving survival, and/or relieving symptoms associated with the cancer. Surgery is the main treatment for RCC that can be removed. (American Cancer Society Kidney Cancer (Adult) Renal Cell Carcinoma Overview.) Even after surgical excision, 20-30% of patients with localized tumors experience relapse, most of which occur within three years. (NCCN Clinical Practice Guidelines in Oncology, Kidney Cancer.) Lung metastasis is the most common site of distant relapse, occurring in 50-60% of patients. (Id.)

If a patient has a small tumor, e.g., <3 cm, however, the physician may not perform surgery, instead opting to monitor the tumor's growth. Such active surveillance may allow some patients to avoid surgery and other treatments. In non-surgical candidates, particularly the elderly and those with competing health risks, ablative techniques, such as cryosurgery or radiofrequency ablation, or active surveillance may be used.

Physicians require prognostic information to help them make informed treatment decisions for patients with RCC and recruit appropriate high risk patients into clinical trials in order to increase the statistical power of the trial. Existing methods are based on subjective measures and therefore may provide inaccurate prognostic information.

SUMMARY

This application discloses molecular assays that involve measurement of expression level(s) of one or more genes or gene subsets from a biological sample obtained from a kidney cancer patient. For example, the likelihood of a clinical outcome may be described in terms of a quantitative score based on observed clinical features of the disease or recurrence-free interval.

In addition, this application discloses methods of obtaining a recurrence score (RS) for a patient with kidney cancer based on measurement of expression level(s) of one or more genes or gene subsets from a biological sample obtained from a kidney cancer patient.

The present disclosure provides a method for obtaining a recurrence score for a patient with kidney cancer comprising measuring a level of at least one RNA transcript, or expression product thereof, in a tumor sample obtained from the patient. The RNA transcript, or expression product thereof, may be selected from APOLD1, EDNRB, NOS3, PPA2B, EIF4EBP1, LMNB1, TUBB2A, CCL5, CEACAM1, CX3CL1, and IL-6. The method comprises normalizing the gene expression level against a level of at least one reference RNA transcript, or expression product thereof, in the tumor sample. In some embodiments, normalization may include compression of gene expression measurements for low expressing genes and/or genes with nonlinear functional forms. The method also comprises assigning the normalized level to a gene subset. The gene subset may be selected from a vascular normalization group, a cell growth/division group, and an immune response group. In some embodiments, APOLD1, EDNRB, NOS3, and PPA2B are assigned to the vascular normalization group. In various embodiments, EIF4EBP1, LMNB1, and TUBB2A are assigned to the cell growth/division group. In other embodiments, CCL5, CEACAM1, and CX3CL1 are assigned to the immune response group. The method also comprises weighting the gene subset according to its contribution to the assessment of risk of cancer recurrence. The method further comprises calculating a recurrence score for the patient using the weighted gene subsets and the normalized levels. The method may further comprise creating a report comprising the recurrence score.

The present disclosure also provides a method of predicting a likelihood of a clinical outcome for a patient with kidney cancer. The method comprises determining a level of one or more RNA transcripts, or an expression product thereof, in a tumor sample obtained from the patient. The one or more RNA transcripts is selected from APOLD1, EDNRB, NOS3, PPA2B, EIF4EBP1, LMNB1, TUBB2A, CCL5, CEACAM1, CX3CL1, and IL-6. The method also comprises assigning the one or more RNA transcripts, or an expression product thereof, to one or more gene subsets. The method also comprises assigning the normalized level to a gene subset. The gene subset may be selected from a vascular normalization group, a cell growth/division group, and an immune response group. In some embodiments, APOLD1, EDNRB, NOS3, and PPA2B are assigned to the vascular normalization group. In various embodiments, EIF4EBP1, LMNB1, and TUBB2A are assigned to the cell growth/division group. In other embodiments, CCL5, CEACAM1, and CX3CL1 are assigned to the immune response group. The method further comprises calculating a quantitative score for the patient by weighting the level of one or more RNA transcripts, or an expression product thereof, by their contribution to the assessment of the likelihood of a clinical outcome. The method additionally comprises predicting a likelihood of a clinical outcome for the patient based on the quantitative score. In some embodiments, an increase in the quantitative score correlates with an increased likelihood of a negative clinical outcome. In some embodiments, the clinical outcome is cancer recurrence.

In some embodiments of the present disclosure, the kidney cancer is renal cell carcinoma. In other embodiments, the kidney cancer is clear cell renal cell carcinoma.

BRIEF DESCRIPTION OF THE DRAWINGS

FIG. 1 shows predictiveness curves and 95% confidence intervals for patients with Stage 1 ccRCC (A) and patients with Stage 2 or Stage 3 ccRCC (B) based on the algorithm described in the Examples.

DETAILED DESCRIPTION

Definitions

Unless defined otherwise, technical and scientific terms used herein have the same meaning as commonly understood by one of ordinary skill in the art to which this invention belongs. Singleton et al., Dictionary of Microbiology and Molecular Biology $2^{nd}$ ed., J. Wiley & Sons (New York, N.Y. 1994), and March, Advanced Organic Chemistry Reactions, Mechanisms and Structure 4th ed., John Wiley & Sons (New York, N.Y. 1992), provide one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described herein. For purposes of the invention, the following terms are defined below.

The terms "tumor" and "lesion" as used herein, refer to all neoplastic cell growth and proliferation, whether malignant or benign, and all pre-cancerous and cancerous cells and tissues.

The terms "cancer," "cancerous," and "carcinoma" refer to or describe the physiological condition in mammals that is typically characterized by unregulated cell growth. Examples of cancer in the present disclosure include cancer of the kidney, such as renal cell carcinoma (RCC, renal cell cancer, or renal cell adenocarcinoma), clear cell renal cell carcinoma, papillary renal cell carcinoma, chromophobe renal cell carcinoma, collecting duct renal cell carcinoma, unclassified renal cell carcinoma, transitional cell carcinoma, Wilms tumor, and renal sarcoma.

As used herein, the terms "kidney cancer," "renal cancer," or "renal cell carcinoma" refer to cancer that has arisen from the kidney.

The terms "renal cell cancer" or "renal cell carcinoma" (RCC), as used herein, refer to cancer which originates in the lining of the proximal convoluted tubule. More specifically, RCC encompasses several relatively common histologic subtypes: clear cell renal cell carcinoma, papillary (chromophil), chromophobe, collecting duct carcinoma, and medullary carcinoma. Clear cell renal cell carcinoma (ccRCC) is the most common subtype of RCC. Incidence of ccRCC is increasing, comprising 80% of localized disease and more than 90% of metastatic disease.

The "pathology" includes all phenomena that compromise the well-being of the patient. This includes, without limitation, abnormal or uncontrollable cell growth, metastasis, interference with the normal functioning of neighboring cells, release of cytokines or other secretory products at abnormal levels, suppression or aggravation of inflammatory or immunological response, neoplasia, premalignancy, malignancy, invasion of surrounding or distant tissues or organs, such as lymph nodes, etc.

The America Joint Committee on Cancer (AJCC) staging system ($7^{th}$ ed., 2010) (also referred to as the TNM (tumor, node, metastasis) system) for kidney cancer uses Roman numerals I through IV (1-4) to describe the extent of the disease. (Edge, S B, et al., AJCC Cancer Staging Manual, ($7^{th}$ Ed. 2010.)) In general, the lower the number, the less the cancer has spread. A higher number, such as stage IV, generally reflects a more serious cancer. The TNM staging system is as follows:

Primary Tumor (T)

Tx Primary tumor cannot be assessed

T0 No evidence of primary tumor

T1 Tumor 7 cm or less in greatest dimension, limited to the kidney

T1a Tumor 4 cm or less in greatest dimension, limited to the kidney

T1b Tumor more than 4 cm but not more than 7 cm in greatest dimension, limited to the kidney T2 Tumor more than 7 cm in greatest dimension, limited to the kidney T2a Tumor more than 7 cm but less than or equal to 10 cm in the greatest dimension, limited to the kidney T2b Tumor more than 10 cm, limited to the kidney T3 Tumor extends into major veins or perinephric tissues but not into the ipsilateral adrenal gland and not beyond Gerota's fascia T3a Tumor grossly extends into the renal vein or its segmental (muscle containing) branches, or tumor invades perirenal and/or renal sinus fat but not beyond Gerota's fascia T3b Tumor grossly extends into the vena cava below the diaphragm T3c Tumor grossly extends into the vena cava above the diaphragm or invades the wall of the vena cava T4 Tumor invades beyond Gerota'a fascia (including contiguous extension into the ipsilateral adrenal gland)

Regional Lymph Nodes (N)

NX Regional lymph nodes cannot be assessed

N0 No regional lymph node metastasis

N1 Metastasis in regional lymph node(s)

Distant Metastasis (M)

M0 No distant metastasis

M1 Distant metastasis

| Anatomic Stage/Prognostic Groups | | | |
| --- | --- | --- | --- |
| Stage I | T1 | N0 | M0 |
| Stage II | T2 | N0 | M0 |
| Stage III | T2 | N0 | M0 |
| Stage IV | T4 | Any N | M0 |
| | Any T | Any N | M1 |

The term "early stage renal cancer", as used herein, refers to Stages 1-3.

Reference to tumor "grade" for renal cell carcinoma as used herein refers to a grading system based on microscopic appearance of tumor cells. According to the TNM staging system of the AJCC, the various grades of renal cell carcinoma are:

GX (grade of differentiation cannot be assessed);

G1 (well differentiated);

G2 (moderately differentiated); and

G3-G4 (poorly differentiated/undifferentiated).

"Increased grade" as used herein refers to classification of a tumor at a grade that is more advanced, e.g., Grade 4 (G4) 4 is an increased grade relative to Grades 1, 2, and 3. Tumor grading is an important prognostic factor in renal cell carcinoma. H. Rauschmeier, et al., World J Urol 2:103-108 (1984).

The terms "necrosis" or "histologic necrosis" as used herein refer to the death of living cells or tissues. The presence of necrosis may be a prognostic factor in cancer. For example, necrosis is commonly seen in renal cell carcinoma (RCC) and has been shown to be an adverse prognostic factor in certain RCC subtypes. V. Foria, et al., J Clin Pathol 58(1):39-43 (2005).

The terms "nodal invasion" or "node-positive (N+)" as used herein refer to the presence of cancer cells in one or more lymph nodes associated with the organ (e.g., drain the organ) containing a primary tumor. Assessing nodal invasion is part of tumor staging for most cancers, including renal cell carcinoma.

The term "prognosis" is used herein to refer to the prediction of the likelihood that a cancer patient will have a cancer-attributable death or progression, including recurrence, metastatic spread, and drug resistance, of a neoplastic disease, such as kidney cancer.

The term "prognostic gene" is used herein to refer to a gene, the expression of which is correlated, positively or negatively, with a likelihood of cancer recurrence in a cancer patient treated with the standard of care. A gene may be both a prognostic and predictive gene, depending on the association of the gene expression level with the corresponding endpoint. For example, using a Cox proportional hazards model, if a gene is only prognostic, its hazard ratio (HR) does not change when measured in patients treated with the standard of care or in patients treated with a new intervention.

The term "prediction" is used herein to refer to the likelihood that a cancer patient will have a particular response to treatment, whether positive ("beneficial response") or negative, following surgical removal of the primary tumor. For example, treatment could include targeted drugs, immunotherapy, or chemotherapy.

The terms "predictive gene" and "response indicator gene" are used interchangeably herein to refer to a gene, the expression level of which is associated, positively or negatively, with likelihood of beneficial response to treatment. A gene may be both a prognostic and predictive gene, and vice versa, depending on the correlation of the gene expression level with the corresponding endpoint (e.g., likelihood of survival without recurrence, likelihood of beneficial response to treatment). A predictive gene can be identified using a Cox proportional hazards model to study the interaction between gene expression levels and the effect of treatment [comparing patients treated with treatment A to patients who did not receive treatment A (but may have received standard of care, e.g. treatment B)]. The hazard ratio (HR) for a predictive gene will change when measured in untreated/standard of care patients versus patients treated with treatment A.

As used herein, the term "expression level" as applied to a gene refers to the normalized level of a gene product, e.g., the normalized value determined for the RNA expression level of a gene or for the polypeptide expression level of a gene.

The term "gene product" or "expression product" are used herein to refer to the RNA transcription products (transcripts) of the gene, including mRNA, and the polypeptide products of such RNA transcripts. A gene product can be, for example, an unspliced RNA, an mRNA, a splice variant mRNA, a microRNA, a fragmented RNA, a polypeptide, a post-translationally modified polypeptide, a splice variant polypeptide, etc.

The term "RNA transcript" as used herein refers to the RNA transcription products of a gene, for example, mRNA, an unspliced RNA, a splice variant mRNA, a micro RNA, and a fragmented RNA.

Unless indicated otherwise, each gene name used herein corresponds to the Official Symbol assigned to the gene and provided by Entrez Gene (URL: www.ncbi.nlm.nih.gov/sites/entrez) as of the filing date of this application.

The terms "correlated" and "associated" are used interchangeably herein to refer to the association between two measurements (or measured entities). The disclosure provides genes and gene subsets, the expression levels of which are associated with a particular outcome measure, such as for example the association between the expression level of a gene and the likelihood of clinical outcome. For example, the increased expression level of a gene may be positively correlated (positively associated) with an increased likelihood of good clinical outcome for the patient, such as an increased likelihood of long-term survival without recurrence of the cancer, and the like. Such a positive correlation may be demonstrated statistically in various ways, e.g. by a low hazard ratio for cancer recurrence or death. In another example, the increased expression level of a gene may be negatively correlated (negatively associated) with an increased likelihood of good clinical outcome for the patient. In that case, for example, the patient may have a decreased likelihood of long-term survival without recurrence of the cancer, and the like. Such a negative correlation indicates that the patient likely has a poor prognosis, and this may be demonstrated statistically in various ways, e.g., a high hazard ratio for cancer recurrence or death. "Correlated" is also used herein to refer to the association between the expression levels of two different genes, such that expression level of a first gene can be substituted with an expression level of a second gene in a given algorithm in view of their correlation of expression. Such "correlated expression" of two genes that are substitutable in an algorithm usually involves gene expression levels that are positively correlated with one another, e.g., if increased expression of a first gene is positively correlated with an outcome (e.g., increased likelihood of good clinical outcome), then the second gene that is co-expressed and exhibits correlated expression with the first gene is also positively correlated with the same outcome.

A "positive clinical outcome" can be assessed using any endpoint indicating a benefit to the patient, including, without limitation, (1) inhibition, to some extent, of tumor growth, including slowing down and complete growth arrest; (2) reduction in the number of tumor cells; (3) reduction in tumor size; (4) inhibition (i.e., reduction, slowing down or complete stopping) of tumor cell infiltration into adjacent peripheral organs and/or tissues; (5) inhibition of metastasis; (6) enhancement of anti-tumor immune response, possibly resulting in regression or rejection of the tumor; (7) relief, to some extent, of one or more symptoms associated with the tumor; (8) increase in the length of survival following treatment; and/or (9) decreased mortality at a given point of time following treatment. Positive clinical response may also be expressed in terms of various measures of clinical outcome. Positive clinical outcome can also be considered in the context of an individual's outcome relative to an outcome of a population of patients having a comparable clinical diagnosis, and can be assessed using various endpoints such as an increase in the duration of Recurrence-Free interval (RFI), an increase in the time of survival as compared to Overall Survival (OS) in a population, an increase in the time of Disease-Free Survival (DFS), an increase in the duration of Distant Recurrence-Free Interval (DRFI), and the like. An increase in the likelihood of positive clinical response corresponds to a decrease in the likelihood of cancer recurrence.

The term "risk classification" means a level of risk (or likelihood) that a subject will experience a particular clinical outcome. A subject may be classified into a risk group or classified at a level of risk based on the methods of the present disclosure, e.g. high, medium, or low risk. A "risk group" is a group of subjects or individuals with a similar level of risk for a particular clinical outcome.

The term "long-term" survival is used herein to refer to survival for a particular period of time, e.g., for at least 3 years, or for at least 5 years.

The terms "recurrence" and "relapse" are used herein, in the context of potential clinical outcomes of cancer, to refer to a local or distant metastases. Identification of a recurrence could be done by, for example, CT imaging, ultrasound, arteriogram, or X-ray, biopsy, urine or blood test, physical exam, or research center tumor registry.

The term "Recurrence-Free Interval (RFI)" is used herein to refer to the time (in years) from randomization to first kidney cancer recurrence or death due to recurrence of kidney cancer.

The term "Overall Survival (OS)" is used herein to refer to the time (in years) from randomization to death from any cause.

The term "Disease-Free Survival (DFS)" is used herein to refer to the time (in years) from randomization to first kidney cancer recurrence or death from any cause.

The calculation of the measures listed above in practice may vary from study to study depending on the definition of events to be either censored or not censored.

The term "Hazard Ratio (HR)" as used herein refers to the effect of an explanatory variable on the hazard or risk of an event (i.e. recurrence or death). In proportional hazards regression models, the HR is the ratio of the predicted hazard for two groups (e.g. patients with two different stages of cancer) or for a unit change in a continuous variable (e.g. one standard deviation change in gene expression).

The term "microarray" refers to an ordered arrangement of hybridizable array elements, e.g., oligonucleotide or polynucleotide probes, on a substrate.

The term "polynucleotide," when used in singular or plural generally refers to any polyribonucleotide or polydeoxyribonucleotide, which may be unmodified RNA or DNA or modified RNA or DNA. Thus, for instance, polynucleotides are defined herein to include, without limitation, single- and double-stranded RNA, and RNA including single- and double-stranded regions, hybrid molecules comprising DNA and RNA that may be single-stranded or, more typically, double-stranded or include single- and double-stranded regions. In addition, the term "polynucleotide" as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. The term "polynucleotide" specifically includes cDNAs. The term includes DNAs (including cDNAs) and RNAs that contain one or more modified bases. Thus, DNAs or RNAs with backbones modified for stability or for other reasons, are "polynucleotides" as that term is intended herein. Moreover, DNAs or RNAs comprising unusual bases, such as inosine, or modified bases, such as tritiated bases, are included within the term "polynucleotides" as defined herein. In general, the term "polynucleotide" embraces all chemically, enzymatically and/or metabolically modified forms of unmodified polynucleotides, as well as the chemical forms of DNA and RNA characteristic of viruses and cells, including simple and complex cells.

The term "oligonucleotide" refers to a relatively short polynucleotide, including, without limitation, single-stranded deoxyribonucleotides, single- or double-stranded ribonucleotides, RNArDNA hybrids and double-stranded DNAs. Oligonucleotides, such as single-stranded DNA probe oligonucleotides, are often synthesized by chemical methods, for example using automated oligonucleotide synthesizers that are commercially available. However, oligonucleotides can be made by a variety of other methods, including in vitro recombinant DNA-mediated techniques and by expression of DNAs in cells and organisms.

As used herein, the term "expression level" as applied to a gene refers to the level of the expression product of a gene, e.g. the normalized value determined for the RNA expression product of a gene or for the polypeptide expression level of a gene.

The term "$C_T$" as used herein refers to threshold cycle, the cycle number in quantitative polymerase chain reaction (qPCR) at which the fluorescence generated within a reaction well exceeds the defined threshold, i.e. the point during the reaction at which a sufficient number of amplicons have accumulated to meet the defined threshold.

The term "Cp" as used herein refers to "crossing point." The Cp value is calculated by determining the second derivatives of entire qPCR amplification curves and their maximum value. The Cp value represents the cycle at which the increase of fluorescence is highest and where the logarithmic phase of a PCR begins.

The terms "threshold" or "thresholding" refer to a procedure used to account for non-linear relationships between gene expression measurements and clinical response as well as to further reduce variation in reported gene expression measurements and patient scores induced by low expressing genes. When thresholding is applied, all measurements below or above a threshold are set to that threshold value. Non-linear relationship between gene expression and outcome could be examined using smoothers or cubic splines to model gene expression in Cox PH regression on recurrence free interval or logistic regression on recurrence status. Variation in reported patient scores could be examined as a function of variability in gene expression at the limit of quantitation and/or detection for a particular gene.

As used herein, the term "amplicon," refers to pieces of DNA that have been synthesized using amplification techniques, such as polymerase chain reactions (PCR) and ligase chain reactions.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to re-anneal when complementary strands are present in an environment below their melting temperature. The higher the degree of desired homology between the probe and hybridizable sequence, the higher the relative temperature which can be used. As a result, it follows that higher relative temperatures would tend to make the reaction conditions more stringent, while lower temperatures less so. For additional details and explanation of stringency of hybridization reactions, see Ausubel et al., Current Protocols in Molecular Biology, Wiley Interscience Publishers, (1995).

"Stringent conditions" or "high stringency conditions", as defined herein, typically: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 g/ml), 0.1% SDS, and 10% dextran sulfate at 42° C., with washes at 42° C. in 0.2×SSC (sodium chloride/sodium citrate) and 50% formamide, followed by a high-stringency wash consisting of 0.1×SSC containing EDTA at 55° C.

"Moderately stringent conditions" may be identified as described by Sambrook et al., Molecular Cloning: A Laboratory Manual, New York: Cold Spring Harbor Press, 1989, and include the use of washing solution and hybridization conditions (e.g., temperature, ionic strength and % SDS) less stringent that those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/ml denatured sheared salmon sperm DNA, followed by washing the filters in 1×SSC at about 37-500 C. The skilled artisan will recognize how to adjust the temperature, ionic strength, etc. as necessary to accommodate factors such as probe length and the like.

The terms "splicing" and "RNA splicing" are used interchangeably and refer to RNA processing that removes introns and joins exons to produce mature mRNA with continuous coding sequence that moves into the cytoplasm of a eukaryotic cell.

As used herein, the term "exon" refers to any segment of an interrupted gene that is represented in the mature RNA product. As used herein, the term "intron" refers to any segment of DNA that is transcribed but removed from within the transcript by splicing together the exons on either side of it. "Intronic RNA" refers to mRNA derived from an intronic region of DNA. Operationally, exonic sequences occur in the mRNA sequence of a gene as defined by Ref. SEQ ID numbers. Operationally, intron sequences are the intervening sequences within the genomic DNA of a gene.

The term "co-expressed", as used herein, refers to a statistical correlation between the expression level of one gene and the expression level of another gene. Pairwise co-expression may be calculated by various methods known in the art, e.g., by calculating Pearson correlation coefficients or Spearman correlation coefficients. Co-expressed gene cliques may also be identified using a graph theory. An analysis of co-expression may be calculated using normalized expression data.

A "computer-based system" refers to a system of hardware, software, and data storage medium used to analyze information. The minimum hardware of a patient computer-based system comprises a central processing unit (CPU), and hardware for data input, data output (e.g., display), and data storage. An ordinarily skilled artisan can readily appreciate that any currently available computer-based systems and/or components thereof are suitable for use in connection with the methods of the present disclosure. The data storage medium may comprise any manufacture comprising a recording of the present information as described above, or a memory access device that can access such a manufacture.

To "record" data, programming or other information on a computer readable medium refers to a process for storing information, using any such methods as known in the art. Any convenient data storage structure may be chosen, based on the means used to access the stored information. A variety of data processor programs and formats can be used for storage, e.g. word processing text file, database format, etc.

A "processor" or "computing means" references any hardware and/or software combination that will perform the functions required of it. For example, a suitable processor may be a programmable digital microprocessor such as available in the form of an electronic controller, mainframe, server or personal computer (desktop or portable). Where the processor is programmable, suitable programming can be communicated from a remote location to the processor, or previously saved in a computer program product (such as a portable or fixed computer readable storage medium, whether magnetic, optical or solid state device based). For example, a magnetic medium or optical disk may carry the programming, and can be read by a suitable reader communicating with each processor at its corresponding station.

The terms "surgery" or "surgical resection" are used herein to refer to surgical removal of some or all of a tumor, and usually some of the surrounding tissue. Examples of surgical techniques include laparoscopic procedures, biopsy, or tumor ablation, such as cryotherapy, radio frequency ablation, and high intensity ultrasound. In cancer patients, the extent of tissue removed during surgery depends on the state of the tumor as observed by a surgeon. For example, a partial nephrectomy indicates that part of one kidney is removed; a simple nephrectomy entails removal of all of one kidney; a radical nephrectomy, all of one kidney and neighboring tissue (e.g., adrenal gland, lymph nodes) removed; and bilateral nephrectomy, both kidneys removed.

Algorithm-Based Methods and Gene Subsets

The present disclosure provides an algorithm-based molecular diagnostic assay for determining an expected clinical outcome, e.g., prognosis. The cancer can be, for example, renal cell carcinoma or clear cell renal cell carcinoma. The present disclosure also provides a method for obtaining a recurrence score for a patient with kidney cancer. For example, the expression levels of the prognostic genes may be used to obtain a recurrence score for a patient with kidney cancer. The algorithm-based assay and associated information provided by the practice of the methods of the present invention facilitate optimal treatment decision-making in kidney cancer. For example, such a clinical tool would enable physicians to identify patients who have a low likelihood of recurrence and therefore may be able to forgo adjuvant treatment. Similarly, such a tool may also enable physicians to identify patients who have a high likelihood of recurrence and who may be good candidates for adjuvant treatment.

As used herein, a "quantitative score" is an arithmetically or mathematically calculated numerical value for aiding in simplifying or disclosing or informing the analysis of more complex quantitative information, such as the correlation of certain expression levels of the disclosed genes or gene subsets to a likelihood of a clinical outcome of a kidney cancer patient. A quantitative score may be determined by the application of a specific algorithm. The algorithm used to calculate the quantitative score in the methods disclosed herein may group the expression level values of genes. The grouping of genes may be performed at least in part based on knowledge of the relative contribution of the genes according to physiologic functions or component cellular characteristics, such as in the groups discussed herein. A quantitative score may be determined for a gene group ("gene group score"). The formation of groups, in addition, can facilitate the mathematical weighting of the contribution of various expression levels of genes or gene subsets to the quantitative score. The weighting of a gene or gene group representing a physiological process or component cellular characteristic can reflect the contribution of that process or characteristic to the pathology of the cancer and clinical outcome, such as recurrence or upgrading/upstaging of the cancer. The present invention provides an algorithm for calculating the quantitative scores, for example, as set forth in the Examples. In an embodiment of the invention, an increase in the quantitative score indicates an increased likelihood of a negative clinical outcome.

In an embodiment, a quantitative score is a "recurrence score," which indicates the likelihood of a cancer recurrence, upgrading or upstaging of a cancer, adverse pathology, non-organ-confined disease, high-grade disease, and/or high-grade or non-organ-confined disease. An increase in the recurrence score may correlate with an increase in the likelihood of cancer recurrence, upgrading or upstaging of a cancer, adverse pathology, non-organ-confined disease, high-grade disease, and/or high-grade or non-organ-confined disease.

The gene subsets of the present invention include a vascular normalization gene group, an immune response gene group, a cell growth/division gene group, and IL-6.

The gene subset identified herein as the "vascular normalization group" includes genes that are involved with vascular and/or angiogenesis functions. The vascular normalization group includes, for example, APOLD1, EDNRB, NOS3, and PPA2B.

The gene subset identified herein as the "cell growth/division group" includes genes that are involved in key cell growth and cell division pathway(s). The cell growth/division group includes, for example, EIF4EBP1, LMNB1, and TUBB2A.

The gene subset identified herein as the "immune response group" includes genes that are involved in functions of the immune system. The immune response group includes, for example, CCL5, CEACAM1, and CX3CL1.

Additionally, expression levels of certain individual genes may be used for calculating the recurrence score. For example, the expression level of IL-6 may be used to calculate the recurrence score. Although IL-6 may be involved in immune responses it may also be involved in other biological processes making it less suitable to be grouped with other immune related genes.

The present invention also provides methods to determine a threshold expression level for a particular gene. A threshold expression level may be calculated for a specific gene. A threshold expression level for a gene may be based on a normalized expression level. In one example, a CT threshold expression level may be calculated by assessing functional forms using logistic regression or Cox proportional hazards regression.

The present invention further provides methods to determine genes that co-express with particular genes identified by, e.g., quantitative RT-PCR (qRT-PCR), as validated biomarkers relevant to a particular type of cancer. The co-expressed genes are themselves useful biomarkers. The co-expressed genes may be substituted for the genes with which they co-express. The methods can include identifying gene cliques from microarray data, normalizing the microarray data, computing a pairwise Spearman correlation matrix for the array probes, filtering out significant co-expressed probes across different studies, building a graph, mapping the probe to genes, and generating a gene clique report. The expression levels of one or more genes of a gene clique may be used to calculate the likelihood that a patient with kidney cancer will experience a positive clinical outcome, such as a reduced likelihood of a cancer recurrence.

Any one or more combinations of gene groups may be assayed in the method of the present invention. For example, a vascular normalization gene group may be assayed, alone or in combination, with a cell growth/division gene group, an immune response gene group, and or 11-6. In addition, any number of genes within each gene group may be assayed.

In a specific embodiment of the invention, a method for predicting a clinical outcome for a patient with kidney cancer comprises measuring an expression level of at least one gene from a vascular normalization gene group, or a co-expressed gene thereof, and at least one gene from a cell growth/division gene group, or a co-expressed gene thereof. In another embodiment, the expression level of at least two genes from a vascular normalization gene group, or a co-expressed gene thereof, and at least two genes from a cell growth/division gene group, or a co-expressed gene thereof, are measured. In yet another embodiment, the expression levels of at least three genes are measured from each of the vascular normalization gene group and the cell growth/division gene group. In a further embodiment, the expression levels of at least four genes from the vascular normalization gene group and at least three genes from the cell growth/differentiation gene group are measured.

In another embodiment of the invention, at least one gene from a vascular normalization gene group, or a co-expressed gene thereof, and at least one gene from an immune response gene group, or a co-expressed gene thereof are measured. In another embodiment, the expression level of at least two genes from a vascular normalization gene group, or a co-expressed gene thereof, and at least two genes from an immune response gene group, or a co-expressed gene thereof, are measured. In yet another embodiment, the expression levels of at least three genes are measured from each of the vascular normalization gene group and the immune response gene group. In a further embodiment, the expression levels of at least four genes from the vascular normalization gene group and at least three genes from the immune response gene group are measured.

In a further embodiment of the invention, an expression level of at least one gene from a vascular normalization gene group, or a co-expressed gene thereof, and IL-6 are measured. In another embodiment, the expression level of at least two genes from a vascular normalization gene group, or a co-expressed gene thereof, and IL-6 are measured. In yet another embodiment, the expression levels of at least three genes from the vascular normalization gene group and IL-6 are measured. In a further embodiment, the expression levels of at least four genes from the vascular normalization gene group and IL-6 are measured.

Additionally, an expression level of at least one gene from a vascular normalization gene group, or a co-expressed gene thereof, and at least one gene from an immune response gene group, or a co-expressed gene thereof is measured. In another embodiment, the expression level of at least two genes from a vascular normalization gene group, or a co-expressed gene thereof, and at least two genes from an immune response gene group, or a co-expressed gene thereof, are measured. In yet another embodiment, the expression levels of at least three genes are measured from each of the vascular normalization gene group and the immune response gene group. In a further embodiment, the expression levels of at least four genes from the vascular normalization gene group and at least three genes from the immune response gene group are measured.

In a specific embodiment of the invention, a method for predicting a clinical outcome for a patient with kidney cancer comprises measuring an expression level of at least one gene from a cell growth/division gene group, or a co-expressed gene thereof, and at least one gene from an immune response gene group, or a co-expressed gene thereof. In another embodiment, the expression level of at least two genes from a cell growth/division gene group, or a co-expressed gene thereof, and at least two genes from an immune response gene group, or a co-expressed gene thereof, are measured. In yet another embodiment, the expression levels of at least three genes are measured from each of the cell growth/division gene group and the immune response gene group.

In a further embodiment of the invention, an expression level of at least one gene from a cell growth/division gene group, or a co-expressed gene thereof, and IL-6 are measured. In another embodiment, the expression level of at least two genes from a cell growth/division gene group, or a co-expressed gene thereof, and IL-6 are measured. In yet another embodiment, the expression levels of at least three genes from the cell growth/division gene group and IL-6 are measured.

In a further embodiment of the invention, an expression level of at least one gene from an immune response gene group, or a co-expressed gene thereof, and IL-6 are measured. In another embodiment, the expression level of at least two genes from an immune response gene group, or a co-expressed gene thereof, and IL-6 are measured. In yet another embodiment, the expression levels of at least three genes from the immune response gene group and IL-6 are measured.

In an additional embodiment of the invention, an expression level of at least one gene from a vascular normalization gene group, or a co-expressed gene thereof, at least one gene from a cell growth/division gene group, or a co-expressed gene thereof, and at least one gene from an immune response gene group are measured. In another embodiment, the expression level of at least two genes from a vascular normalization gene group, or a co-expressed gene thereof, at least two genes from a cell growth/division gene group, or a co-expressed gene thereof, and at least two genes from an immune response gene group are measured. In yet another embodiment, the expression levels of at least three genes are measured from each of the vascular normalization gene group, the cell growth/division gene group, and the immune response gene group. In a further embodiment, the expression levels of at least four genes from the vascular normalization gene group, at least three genes from the cell growth/differentiation gene group, and at least three genes from the immune response gene group are measured.

In another embodiment of the invention, an expression level of at least one gene from a vascular normalization gene group, or a co-expressed gene thereof, at least one gene from a cell growth/division gene group, or a co-expressed gene thereof, at least one gene from an immune response gene group, and IL-6 are measured. In another embodiment, the expression level of at least two genes from a vascular normalization gene group, or a co-expressed gene thereof, at least two genes from a cell growth/division gene group, or a co-expressed gene thereof, at least two genes from an immune response gene group, and IL-6 are measured. In yet another embodiment, the expression levels of at least three genes are measured from each of the vascular normalization gene group, the cell growth/division gene group, and the immune response gene group, and IL-6. In a further embodiment, the expression levels of at least four genes from the vascular normalization gene group, at least three genes from the cell growth/differentiation gene group, at least three genes from the immune response gene group, and IL-6 are measured.

Additionally, expression levels of one or more genes that do not fall within the gene subsets described herein may be measured with any of the combinations of the gene subsets described herein. Alternatively, any gene that falls within a gene subset may be analyzed separately from the gene subset, or in another gene subset.

In a specific embodiment, the method of the invention comprises measuring the expression levels of the specific combinations of genes and gene subsets shown in the Examples. In a further embodiment, gene group score(s) and quantitative score(s) are calculated according to the algorithm(s) shown in the Examples. In certain embodiments, the method of the invention comprises measuring expression levels of the cancer-related genes APOLD1, CCL5, CEACAM1, CX3CL1, EDNRB, EIF4EBP 1, IL6, LMNB 1, NOS3, PPAP2B, and TUBB2A, and the reference genes AAMP, ARF1, ATP5E, GPX1, and RPLP1, normalizing the expression levels of one or more of the cancer-related genes against the expression levels of one or more of the reference genes, assigning the normalized expression levels to gene subsets, weighting the gene subset according to its contribution to cancer recurrence, calculating a recurrence score using the weighted gene subset and the normalized levels, and creating a report comprising the recurrence score.

In certain embodiments, the method of the invention comprises measuring expression levels of certain subgroups of cancer-related genes selected from the group consisting of: (1) APOLD1, NOS3, and EMCN; (2) APOLD1, NOS3, IL6, IL8, and EMCN; (3) CEACAM1, CX3CL1, IL6, and IL8; (4) EIF4EBP1 and LMNB1; (5) APOLD1, EDNRB, and NOS3; (6) APOLD1, EDNRB, and PPAP2B; (7) APOLD1, NOS3, and PPAP2B; (8) EDNRB, NOS3, and PPAP2B; (9) APOLD1 and NOS3; (10) NOS3 and PPAP2B; (11) APOLD1, NOS3, PPAP2B, and CEACAM1; (12) APOLD1, NOS3, PPAP2B, and CX3CL1; (13) APOLD1, NOS3, CEACAM1, and CX3CL1; (14) APOLD1, PPAP2B, CEACAM1, and CX3CL1; (15) NOS3, PPAP2B, CEACAM1, and CX3CL1; (16) APOLD1, NOS3, CEACAM1, CX3CL1, and EIF4EBP1; (17) NOS3, PPAP2B, CEACAM1, CX3CL1, and EIF4EBP1; (18) APOLD1, NOS3, CEACAM1, CX3CL1, and LMNB1; (19) NOS3, PPAP2B, CEACAM1, CX3CL1, and LMNB1; (20) APOLD1, NOS3, CEACAM1, CX3CL1, and TUBB2A; and (21) NOS3, PPAP2B, CEACAM1, CX3CL1, and TUBB2A and the reference genes AAMP, ARF1, ATP5E, GPX1, and RPLP1, normalizing the expression levels of one or more of the subgroups of cancer-related genes against the expression levels of one or more of the reference genes, and creating a report comprising the risk of recurrence. In certain embodiments, the risk of recurrence is estimated from a hazard ratio calculated using the normalized expression levels of one or more subgroups of cancer-related genes.

Various technological approaches for determination of expression levels of the disclosed genes are set forth in this specification, including, without limitation, RT-PCR, microarrays, high-throughput sequencing, serial analysis of gene expression (SAGE) and Digital Gene Expression (DGE), which will be discussed in detail below. In particular aspects, the expression level of each gene may be determined in relation to various features of the expression products of the gene including exons, introns, protein epitopes and protein activity.

The expression product that is assayed can be, for example, RNA or a polypeptide. The expression product may be fragmented. For example, the assay may use primers that are complementary to target sequences of an expression product and could thus measure full transcripts as well as those fragmented expression products containing the target sequence. Further information is provided in Tables A and B.

The RNA expression product may be assayed directly or by detection of a cDNA product resulting from a PCR-based amplification method, e.g., quantitative reverse transcription polymerase chain reaction (qRT-PCR). (See e.g., U.S. Pat. No. 7,587,279). Polypeptide expression product may be assayed using immunohistochemistry (IHC) by proteomics techniques. Further, both RNA and polypeptide expression products may also be assayed using microarrays.

Clinical Utility

Currently, of the expected clinical outcome for RCC patients is based on subjective determinations of a tumor's clinical and pathologic features. For example, physicians make decisions about the appropriate surgical procedures and adjuvant therapy based on a renal tumor's stage, grade, and the presence of necrosis. Although there are standardized measures to guide pathologists in making these decisions, the level of concordance between pathology laboratories is low. (See Al-Ayanti M et al. (2003) Arch Pathol Lab Med 127, 593-596) It would be useful to have a reproducible molecular assay for determining and/or confirming these tumor characteristics.

In addition, standard clinical criteria, by themselves, have limited ability to accurately estimate a patient's prognosis. It would be useful to have a reproducible molecular assay to assess a patient's prognosis based on the biology of his or her tumor. Such information could be used for the purposes of patient counseling, selecting patients for clinical trials (e.g., adjuvant trials), and understanding the biology of renal cell carcinoma. In addition, such a test would assist physicians in making surgical and treatment recommendations based on the biology of each patient's tumor. For example, a genomic test could stratify RCC patients based on risk of recurrence and/or likelihood of long-term survival without recurrence (relapse, metastasis, etc.). There are several ongoing and planned clinical trials for RCC therapies, including adjuvant radiation and chemotherapies. It would be useful to have a genomic test able to identify high-risk patients more accurately than standard clinical criteria, thereby further enriching an adjuvant RCC population for study. This would reduce the number of patients needed for an adjuvant trial and the time needed for definitive testing of these new agents in the adjuvant setting.

Finally, it would be useful to have a molecular assay that could predict a patient's likelihood to respond to specific treatments. Again, this would facilitate individual treatment decisions and recruiting patients for clinical trials, and increase physician and patient confidence in making healthcare decisions after being diagnosed with cancer.

Methods of Assaying Expression Levels of a Gene Product

Methods of expression profiling include methods based on sequencing of polynucleotides, methods based on hybridization analysis of polynucleotides, and proteomics-based methods. Representative methods for sequencing-based analysis include Massively Parallel Sequencing (see e.g., Tucker et al., The American J. Human Genetics 85:142-154, 2009) and Serial Analysis of Gene Expression (SAGE). Exemplary methods known in the art for the quantification of mRNA expression in a sample include northern blotting and in situ hybridization (Parker & Barnes, Methods in Molecular Biology 106:247-283 (1999)); RNase protection assays (Hod, Biotechniques 13:852-854 (1992)); and PCR-based methods, such as reverse transcription polymerase chain reaction (RT-PCR) (Weis et al., Trends in Genetics 8:263-264 (1992)). Antibodies may be employed that can recognize sequence-specific duplexes, including DNA duplexes, RNA duplexes, and DNA-RNA hybrid duplexes or DNA-protein duplexes.

Nucleic Acid Sequencing-Based Methods

Nucleic acid sequencing technologies are suitable methods for expression analysis. The principle underlying these methods is that the number of times a cDNA sequence is detected in a sample is directly related to the relative RNA levels corresponding to that sequence. These methods are sometimes referred to by the term Digital Gene Expression (DGE) to reflect the discrete numeric property of the resulting data. Early methods applying this principle were Serial Analysis of Gene Expression (SAGE) and Massively Parallel Signature Sequencing (MPSS). See, e.g., S. Brenner, et al., Nature Biotechnology 18(6):630-634 (2000).

More recently, the advent of "next-generation" sequencing technologies has made DGE simpler, higher throughput, and more affordable. As a result, more laboratories are able to utilize DGE to screen the expression of more nucleic acids in more individual patient samples than previously possible. See, e.g., J. Marioni, Genome Research 18(9):1509-1517 (2008); R. Morin, Genome Research 18(4):610-621 (2008); A. Mortazavi, Nature Methods 5(7):621-628 (2008); N. Cloonan, Nature Methods 5(7):613-619 (2008). Massively parallel sequencing methods have also enabled whole genome or transcriptome sequencing, allowing the analysis of not only coding but also non-coding sequences. As reviewed in Tucker et al., The American J. Human Genetics 85:142-154 (2009), there are several commercially available massively parallel sequencing platforms, such as the Illumina Genome Analyzer (Illumina, Inc., San Diego, Calif.), Applied Biosystems SOLiD™ Sequencer (Life Technologies, Carlsbad, Calif.), Roche GS-FLX 454 Genome Sequencer (Roche Applied Science, Germany), and the Helicos® Genetic Analysis Platform (Helicos Biosciences Corp., Cambridge, Mass.). Other developing technologies may be used.

Reverse Transcription PCR (RT-PCR)

The starting material is typically total RNA isolated from a human tumor, usually from a primary tumor. Optionally, normal tissues from the same patient can be used as an internal control. RNA can be extracted from a tissue sample, e.g., from a sample that is fresh, frozen (e.g. fresh frozen), or paraffin-embedded and fixed (e.g. formalin-fixed).

General methods for RNA extraction are well known in the art and are disclosed in standard textbooks of molecular biology, including Ausubel et al., Current Protocols of Molecular Biology, John Wiley and Sons (1997). Methods for RNA extraction from paraffin embedded tissues are disclosed, for example, in Rupp and Locker, Lab Invest. 56:A67 (1987), and De Andres et al., BioTechniques 18:42044 (1995). In particular, RNA isolation can be performed using a purification kit, buffer set and protease from commercial manufacturers, such as Qiagen, according to the manufacturer's instructions. For example, total RNA from cells in culture can be isolated using Qiagen RNeasy mini-columns. Other commercially available RNA isolation kits include MasterPure™ Complete DNA and RNA Purification Kit (EPICENTRE®, Madison, Wis.), and Paraffin Block RNA Isolation Kit (Ambion, Inc.). Total RNA from tissue samples can be isolated using RNA Stat-60 (Tel-Test). RNA prepared from a tumor sample can be isolated, for example, by cesium chloride density gradient centrifugation. The isolated RNA may then be depleted of ribosomal RNA as described in U.S. Pub. No. 2011/0111409.

The sample containing the RNA is then subjected to reverse transcription to produce cDNA from the RNA template, followed by exponential amplification in a PCR reaction. The two most commonly used reverse transcriptases are avian myeloblastosis virus reverse transcriptase (AMV-RT) and Moloney murine leukemia virus reverse transcriptase (MMLV-RT). The reverse transcription step is typically primed using specific primers, random hexamers, or oligo-dT primers, depending on the circumstances and the goal of expression profiling. For example, extracted RNA can be reverse-transcribed using a GeneAmp RNA PCR kit (Perkin Elmer, Calif., USA), following the manufacturer's instructions. The derived cDNA can then be used as a template in the subsequent PCR reaction.

PCR-based methods use a thermostable DNA-dependent DNA polymerase, such as a Taq DNA polymerase. For example, TaqMan® PCR typically utilizes the 5'-nuclease activity of Taq or Tth polymerase to hydrolyze a hybridization probe bound to its target amplicon, but any enzyme with equivalent 5' nuclease activity can be used. Two oligonucleotide primers are used to generate an amplicon typical of a PCR reaction product. A third oligonucleotide, or probe, can be designed to facilitate detection of a nucleotide sequence of the amplicon located between the hybridization sites of the two PCR primers. The probe can be detectably labeled, e.g., with a reporter dye and can further be provided with both a fluorescent dye, and a quencher fluorescent dye, as in a TaqMan® probe configuration. Where a TaqMan® probe is used, during the amplification reaction, the Taq DNA polymerase enzyme cleaves the probe in a template-dependent manner. The resultant probe fragments disassociate in solution, and signal from the released reporter dye is free from the quenching effect of the second fluorophore. One molecule of reporter dye is liberated for each new molecule synthesized, and detection of the unquenched reporter dye provides the basis for quantitative interpretation of the data.

TaqMan® RT-PCR can be performed using commercially available equipment, such as, for example, ABI PRISM 7700TM Sequence Detection System™ (Perkin-Elmer-Applied Biosystems, Foster City, Calif., USA), or LightCycler (Roche Molecular Biochemicals, Mannheim, Germany). In a preferred embodiment, the 5' nuclease procedure is run on a real-time quantitative PCR device such as the ABI PRISM 7700TM Sequence Detection System™. The system consists of a thermocycler, laser, charge-coupled device (CCD), camera and computer. The system amplifies samples in a 384-well format on a thermocycler. The RT-PCR may be performed in triplicate wells with an equivalent of 2 ng RNA input per 10 μL-reaction volume. During amplification, laser-induced fluorescent signal is collected in real-time through fiber optics cables for all wells, and detected at the CCD. The system includes software for running the instrument and for analyzing the data.

5'-Nuclease assay data are generally initially expressed as a threshold cycle ("$C_T$"). Fluorescence values are recorded during every cycle and represent the amount of product amplified to that point in the amplification reaction. The threshold cycle ($C_T$) is generally described as the point when the fluorescent signal is first recorded as statistically significant. The Cp value is calculated by determining the second derivatives of entire qPCR amplification curves and their maximum value. The Cp value represents the cycle at which the increase of fluorescence is highest and where the logarithmic phase of a PCR begins.

To minimize errors and the effect of sample-to-sample variation, RT-PCR is usually performed using an internal standard. The ideal internal standard gene (also referred to as a reference gene) is expressed at a constant level among cancerous and non-cancerous tissue of the same origin (i.e., a level that is not significantly different among normal and cancerous tissues), and is not significantly affected by the experimental treatment (i.e., does not exhibit a significant difference in expression level in the relevant tissue as a result of exposure to chemotherapy). RNAs most frequently used to normalize patterns of gene expression are mRNAs for the housekeeping genes glyceraldehyde-3-phosphate-dehydrogenase (GAPDH) and β-actin. Gene expression measurements can be normalized relative to the mean of one or more (e.g., 2, 3, 4, 5, or more) reference genes. Reference-normalized expression measurements can range from 0 to 15, where a one unit increase generally reflects a 2-fold increase in RNA quantity.

Real time PCR is compatible both with quantitative competitive PCR, where an internal competitor for each target sequence is used for normalization, and with quantitative comparative PCR using a normalization gene contained within the sample, or a housekeeping gene for RT-PCR. For further details see, e.g. Held et al., Genome Research 6:986-994 (1996).

Design of PCR Primers and Probes

PCR primers and probes can be designed based upon exon, intron, or intergenic sequences present in the RNA transcript of interest. Primer/probe design can be performed using publicly available software, such as the DNA BLAT software developed by Kent, W. J., Genome Res. 12(4):656-64 (2002), or by the BLAST software including its variations.

Where necessary or desired, repetitive sequences of the target sequence can be masked to mitigate non-specific signals. Exemplary tools to accomplish this include the Repeat Masker program available on-line through the Baylor College of Medicine, which screens DNA sequences against a library of repetitive elements and returns a query sequence in which the repetitive elements are masked. The masked sequences can then be used to design primer and probe sequences using any commercially or otherwise publicly available primer/probe design packages, such as Primer Express (Applied Biosystems); MGB assay-by-design (Applied Biosystems); Primer3 (Steve Rozen and Helen J. Skaletsky (2000) Primer3 on the WWW for general users and for biologist programmers. In: Rrawetz S, Misener S (eds) Bioinformatics Methods and Protocols: Methods in Molecular Biology. Humana Press, Totowa, N.J., pp 365-386).

Other factors that can influence PCR primer design include primer length, melting temperature (Tm), and G/C content, specificity, complementary primer sequences, and 3'-end sequence. In general, optimal PCR primers are generally 17-30 bases in length, and contain about 20-80%, such as, for example, about 50-60% G+C bases, and exhibit Tm's between 50 and 80° C., e.g. about 50 to 70° C.

For further guidelines for PCR primer and probe design see, e.g. Dieffenbach, C W. et al, "General Concepts for PCR Primer Design" in: PCR Primer, A Laboratory Manual, Cold Spring Harbor Laboratory Press, N.Y., 1995, pp. 133-155; Innis and Gelfand, "Optimization of PCRs" in: PCR Protocols, A Guide to Methods and Applications, CRC Press, London, 1994, pp. 5-11; and Plasterer, T. N. Primerselect: Primer and probe design. Methods Mol. Biol. 70:520-527 (1997), the entire disclosures of which are hereby expressly incorporated by reference.

Tables A and B provide further information concerning the primer, probe, and amplicon sequences associated with the Examples disclosed herein.

MassARRAY® System

In MassARRAY-based methods, such as the exemplary method developed by Sequenom, Inc. (San Diego, Calif.) following the isolation of RNA and reverse transcription, the obtained cDNA is spiked with a synthetic DNA molecule (competitor), which matches the targeted cDNA region in all positions, except a single base, and serves as an internal standard. The cDNA/competitor mixture is PCR amplified and is subjected to a post-PCR shrimp alkaline phosphatase (SAP) enzyme treatment, which results in the dephosphorylation of the remaining nucleotides. After inactivation of the alkaline phosphatase, the PCR products from the competitor and cDNA are subjected to primer extension, which generates distinct mass signals for the competitor- and cDNA-derived PCR products. After purification, these products are dispensed on a chip array, which is pre-loaded with components needed for analysis with matrix-assisted laser desorption ionization time-of-flight mass spectrometry (MALDI-TOF MS) analysis. The cDNA present in the reaction is then quantified by analyzing the ratios of the peak areas in the mass spectrum generated. For further details see, e.g. Ding and Cantor, Proc. Natl. Acad. Sci. USA 100:3059-3064 (2003).

Other PCR-Based Methods

Further PCR-based techniques that can find use in the methods disclosed herein include, for example, BeadArray® technology (Illumina, San Diego, Calif.; Oliphant et al., Discovery of Markers for Disease (Supplement to Biotechniques), June 2002; Ferguson et al., Analytical Chemistry 72:5618 (2000)); BeadsArray for Detection of Gene Expression® (BADGE), using the commercially available Luminex1OO LabMAP® system and multiple color-coded microspheres (Luminex Corp., Austin, Tex.) in a rapid assay for gene expression (Yang et al., Genome Res. 11:1888-1898 (2001)); and high coverage expression profiling (HiCEP) analysis (Fukumura et al., Nucl. Acids. Res. 31(16) e94 (2003).

Microarrays

In this method, polynucleotide sequences of interest (including cDNAs and oligonucleotides) are arrayed on a substrate. The arrayed sequences are then contacted under conditions suitable for specific hybridization with detectably labeled cDNA generated from RNA of a sample. The source of RNA typically is total RNA isolated from a tumor sample, and optionally from normal tissue of the same patient as an internal control or cell lines. RNA can be extracted, for example, from frozen or archived paraffin-embedded and fixed (e.g. formalin-fixed) tissue samples.

For example, PCR amplified inserts of cDNA clones of a gene to be assayed are applied to a substrate in a dense array. Usually at least 10,000 nucleotide sequences are applied to the substrate. For example, the microarrayed genes, immobilized on the microchip at 10,000 elements each, are suitable for hybridization under stringent conditions. Fluorescently labeled cDNA probes may be generated through incorporation of fluorescent nucleotides by reverse transcription of RNA extracted from tissues of interest. Labeled cDNA probes applied to the chip hybridize with specificity to each spot of DNA on the array. After washing under stringent conditions to remove non-specifically bound probes, the chip is scanned by confocal laser microscopy or by another detection method, such as a CCD camera. Quantitation of hybridization of each arrayed element allows for assessment of corresponding mRNA abundance.

With dual color fluorescence, separately labeled cDNA probes generated from two sources of RNA are hybridized pair wise to the array. The relative abundance of the transcripts from the two sources corresponding to each specified gene is thus determined simultaneously. The miniaturized scale of the hybridization affords a convenient and rapid evaluation of the expression pattern for large numbers of genes. Such methods have been shown to have the sensitivity required to detect rare transcripts, which are expressed at a few copies per cell, and to reproducibly detect at least approximately two-fold differences in the expression levels (Schena et at, Proc. Natl. Acad. Sci. USA 93(2):106-149 (1996)). Microarray analysis can be performed on commercially available equipment, following the manufacturer's protocols, such as by using the Affymetrix GenChip® technology, or Incyte's microarray technology.

Isolating RNA from Body Fluids

Methods of isolating RNA for expression analysis from blood, plasma and serum (see for example, Tsui NB et al. (2002) Clin. Chem. 48, 1647-53 and references cited therein) and from urine (see for example, Boom R et al. (1990) J Clin Microbiol. 28, 495-503 and reference cited therein) have been described.

Methods of Isolating RNA from Paraffin-Embedded Tissue

The steps of a representative protocol for profiling gene expression using fixed, paraffin-embedded tissues as the RNA source, including mRNA isolation, purification primer extension and amplification are provided in various published journal articles. (See, e.g., T. E. Godfrey et al,. J. Molec. Diagnostics 2: 84-91 (2000); K. Specht et al., Am. J. Pathol. 158: 419-29 (2001), M. Cronin, et al., Am J Pathol 164:35-42 (2004)).

Immunohistochemistry

Immunohistochemistry methods are also suitable for detecting the expression levels of genes and applied to the method disclosed herein. Antibodies (e.g., monoclonal antibodies) that specifically bind a gene product of a gene of interest can be used in such methods. The antibodies can be detected by direct labeling of the antibodies themselves, for example, with radioactive labels, fluorescent labels, hapten labels such as, biotin, or an enzyme such as horse radish peroxidase or alkaline phosphatase. Alternatively, unlabeled primary antibody can be used in conjunction with a labeled secondary antibody specific for the primary antibody. Immunohistochemistry protocols and kits are well known in the art and are commercially available.

Proteomics

The term "proteome" is defined as the totality of the proteins present in a sample (e.g. tissue, organism, or cell culture) at a certain point of time. Proteomics includes, among other things, study of the global changes of protein expression in a sample (also referred to as "expression proteomics"). Proteomics typically includes the following steps: (1) separation of individual proteins in a sample by 2-D gel electrophoresis (2-D PAGE); (2) identification of the individual proteins recovered from the gel, e.g. my mass spectrometry or N-terminal sequencing, and (3) analysis of the data using bioinformatics.

General Description of the mRNA Isolation, Purification and Amplification

The steps of a representative protocol for profiling gene expression using fixed, paraffin-embedded tissues as the RNA source, including mRNA isolation, purification, primer extension and amplification are provided in various published journal articles. (See, e.g., T. E. Godfrey, et al,. J. Molec. Diagnostics 2: 84-91 (2000); K. Specht et al., Am. J. Pathol. 158: 419-29 (2001), M. Cronin, et al., Am J Pathol 164:35-42 (2004)). Briefly, a representative process starts with cutting a tissue sample section (e.g. about 10 µm thick sections of a paraffin-embedded tumor tissue sample). The RNA is then extracted, and protein and DNA are removed. After analysis of the RNA concentration, RNA repair is performed if desired. The sample can then be subjected to analysis, e.g., by reverse transcribed using gene specific promoters followed by RT-PCR.

Statistical Analysis of Gene Expression Levels in Identification of Marker Genes for Use in Prognostic Methods One skilled in the art will recognize that there are many statistical methods that may be used to determine whether there is a significant relationship between an outcome of interest (e.g., likelihood of survival, likelihood of response to chemotherapy) and expression levels of a marker gene as described here. This relationship can be presented as a continuous recurrence score (RS), or patients may be stratified into risk groups (e.g., low, intermediate, high). For example, a Cox proportional hazards regression model may provide an adequate fit to a particular clinical endpoint (e.g., RFI, DFS, OS). One assumption of the Cox proportional hazards regression model is the proportional hazards assumption, i.e. the assumption that effect parameters multiply the underlying hazard. Assessments of model adequacy may be performed including, but not limited to, examination of the cumulative sum of martingale residuals. One skilled in the art would recognize that there are numerous statistical methods that may be used (e.g., Royston and Parmer (2002), smoothing spline, etc.) to fit a flexible parametric model using the hazard scale and the Weibull distribution with natural spline smoothing of the log cumulative hazards function, with effects for treatment (chemotherapy or observation) and RS allowed to be time-dependent. (See, P. Royston, M. Parmer, Statistics in Medicine 21(15:2175-2197 (2002).) The relationship between recurrence risk and (1) recurrence risk groups; and (2) clinical/pathologic covariates (e.g., number of nodes examined, pathological T stage, tumor grade, lymphatic or vascular invasion, etc.) may also be tested for significance.

In an exemplary embodiment, power calculations were carried for the Cox proportional hazards model with a single non-binary covariate using the method proposed by F. Hsieh and P. Lavori, Control Clin Trials 21:552-560 (2000) as implemented in PASS 2008.

General Description of Exemplary Embodiments

This disclosure provides a method for obtaining a recurrence score for a patient with kidney cancer by assaying expression levels of certain prognostic genes from a tumor sample obtained from the patient. Such methods involve use of gene subsets that are created based on similar functions of gene products. For example, prognostic methods disclosed herein involve assaying expression levels of gene subsets that include at least one gene from each of a vascular normalization group, an immune response group, and cell growth/division group, and IL-6, and calculating a recurrence score (RS) for the patient by weighting the expression levels of each of the gene subsets by their respective contributions to cancer recurrence. The weighting may be different for each gene subset, and may be either positive or negative. For example, the vascular normalization gene group score may be weighted by multiplying a factor of −0.45, the immune response gene group score may be weighted by multiplying a factor of −0.31, the cell growth/division gene group score may be weighted by a factor of +0.27, and the value for IL-6 may be multiplied by a factor of +0.04.

Normalization of Expression Levels

The expression data used in the methods disclosed herein can be normalized. Normalization refers to a process to correct for (normalize away), for example, differences in the amount of RNA assayed and variability in the quality of the RNA used, to remove unwanted sources of systematic variation in CT measurements, and the like. With respect to RT-PCR experiments involving archived fixed paraffin embedded tissue samples, sources of systematic variation are known to include the degree of RNA degradation relative to the age of the patient sample and the type of fixative used to store the sample. Other sources of systematic variation may be attributable to laboratory processing conditions.

Assays can provide for normalization by incorporating the expression of certain normalizing genes, which genes are relatively invariant under the relevant conditions. Exemplary normalization genes include housekeeping genes. Normalization can be based on the mean or median signal (CT) of all of the assayed genes or a large subset thereof (global normalization approach). In general, the normalizing genes, also referred to as reference genes should be genes that are known to be invariant in kidney cancer as compared to non-cancerous kidney tissue, and are not significantly affected by various sample and process conditions, thus provide for normalizing away extraneous effects.

Unless noted otherwise, normalized expression levels for each mRNA/tested tumor/patient will be expressed as a percentage of the expression level measured in the reference set. A reference set of a sufficiently high number (e.g., 40) of tumors yields a distribution of normalized levels of each mRNA species. The level measured in a particular tumor sample to be analyzed falls at some percentile within this range, which can be determined by methods well known in the art.

In exemplary embodiments, one or more of the following genes are used as references by which the expression data is normalized: AAMP, ARF1, ATP5E, GPX1, and RPLP1. The calibrated weighted average CT measurements for each of the prognostic genes may be normalized relative to the mean of five or more reference genes.

Those skilled in the art will recognize that normalization may be achieved in numerous ways, and the techniques described above are intended only to be exemplary, not exhaustive.

Standardization of Expression Levels

The expression data used in the methods disclosed herein can be standardized. Standardization refers to a process to effectively put all the genes on a comparable scale. This is performed because some genes will exhibit more variation (a broader range of expression) than others. Standardization is performed by dividing each expression value by its standard deviation across all samples for that gene. Hazard ratios are then interpreted as the proportional change in the hazard for the clinical endpoint (clinical recurrence, biological recurrence, death due to kidney cancer, or death due to any cause) per 1 standard deviation increase in expression.

Bridging Expression Measurements and Calibration

An oligonucleotide set represents a forward primer, reverse primer, and probe that are used to build a primer and probe (P3) pool and gene specific primer (GSP) pool. Systematic differences in RT-PCR cycle threshold ($C_T$) measurements can result between different oligonucleotide sets due to inherent variations oligonucleotide syntheses. For example, differences in oligonucleotide sets may exist between development, production (used for validation), and future production nucleotide sets. Thus, use of statistical calibration procedures to adjust for systematic differences in oligonucleotide sets resulting in translation in the gene coefficients used in calculating RS may be desirable. For example, for each of the genes assayed for use in an algorithm, one may use a scatterplot of CT measurements for production oligonucleotide sets versus $C_T$ measurements from a corresponding sample used in different oligonucleotide set to create linear regression model that treats the effect of lot-to-lot differences as a random effect. Examination of such a plot will reveal that the variance of CT measurements increases exponentially as a function of the mean $C_T$. The random effects linear regression model can be evaluated with log-linear variance, to obtain a linear calibration equation. A calculated mean squared error (MSE) for the scores can be compared to the MSE if no calibration scheme is used at all.

As another example, a latent variable measurement of $C_T$ (e.g. first principle component) may be derived from various oligonucleotide sets. The latent variable is a reasonable measure of the "true" underlying $C_T$ measurement. Similar to the method described above, a linear regression model may be fit to the sample pairs treating the effects of differences as a random effect, and the weighted average $C_T$ value adjusted to a calibrated $C_T$.

Centering and Data Compression/Scaling

Systematic differences in the distribution of patient RS due to analytical or sample differences may exist between early development, clinical validation and commercial samples. A constant centering tuning parameter may be used in the algorithm to account for such difference.

Data compression is a procedure used to reduce the variability in observed normalized $C_T$ values beyond the limit of quantitation (LOQ) of the assay. Specifically, for each of the kidney cancer assay genes, variance in $C_T$ measurements increase exponentially as the normalized $C_T$ for a gene extends beyond the LOQ of the assay. To reduce such variation, normalized $C_T$ values for each gene may be compressed towards the LOQ of the assay. Additionally, normalized $C_T$ values may be rescaled. For example, normalized $C_T$ values of the prognostic and reference genes may be rescaled to a range of 0 to 15, where a one-unit increase generally reflects a 2-fold increase in RNA quantity.

Threshold Values

The present invention describes a method to determine a threshold value for expression of a cancer-related gene, comprising measuring an expression level of a gene, or its expression product, in a tumor section obtained from a cancer patient, normalizing the expression level to obtain a normalized expression level, calculating a threshold value for the normalized expression level, and determining a score based on the likelihood of recurrence or clinically beneficial response to treatment, wherein if the normalized expression level is less than the threshold value, the threshold value is used to determine the score, and wherein if the normalized expression level is greater or equal to the threshold value, the normalized expression level is used to determine the score.

For example, a threshold value for each cancer-related gene may be determined through examination of the functional form of relationship between gene expression and outcome. Examples of such analyses are presented for Cox PH regression on recurrence free interval where gene expression is modeled using natural splines and for logistic regression on recurrence status where gene expression is modeled using a lowess smoother.

In some embodiments, if the relationship between the term and the risk of recurrence is non-linear or expression of the gene is relatively low, a threshold may be used. In an embodiment, when the expression of IL6 is <4 $C_T$ the value is fixed at 4 $C_T$.

Kits of the Invention

The materials for use in the methods of the present invention are suited for preparation of kits produced in accordance with well-known procedures. The present disclosure thus provides kits comprising agents, which may include gene-specific or gene-selective probes and/or primers, for quantitating the expression of the disclosed genes for predicting prognostic outcome or response to treatment. Such kits may optionally contain reagents for the extraction of RNA from tumor samples, in particular fixed paraffin-embedded tissue samples and/or reagents for RNA amplification. In addition, the kits may optionally comprise the reagent(s) with an identifying description or label or instructions relating to their use in the methods of the present invention. The kits may comprise containers (including microliter plates suitable for use in an automated implementation of the method), each with one or more of the various reagents (typically in concentrated form) utilized in the methods, including, for example, pre-fabricated microarrays, buffers, the appropriate nucleotide triphosphates (e.g., dATP, dCTP, dGTP and dTTP; or rATP, rCTP, rGTP and UTP), reverse transcriptase, DNA polymerase, RNA polymerase, and one or more probes and primers of the present invention (e.g., appropriate length poly(T) or random primers linked to a promoter reactive with the RNA polymerase). Mathematical algorithms used to estimate or quantify prognostic or predictive information are also properly potential components of kits.

Reports

The methods of this invention, when practiced for commercial diagnostic purposes, generally produce a report or summary of information obtained from the herein-described methods. For example, a report may include information concerning expression levels of prognostic genes, a Recurrence Score, a prediction of the predicted clinical outcome for a particular patient, or thresholds. The methods and reports of this invention can further include storing the report in a database. The method can create a record in a database for the subject and populate the record with data. The report may be a paper report, an auditory report, or an electronic record. The report may be displayed and/or stored on a computing device (e.g., handheld device, desktop computer, smart device, website, etc.). It is contemplated that the report is provided to a physician and/or the patient. The receiving of the report can further include establishing a network connection to a server computer that includes the data and report and requesting the data and report from the server computer.

Computer Program

The values from the assays described above, such as expression data, recurrence score, treatment score and/or benefit score, can be calculated and stored manually. Alternatively, the above-described steps can be completely or partially performed by a computer program product. The present invention thus provides a computer program product including a computer readable storage medium having a computer program stored on it. The program can, when read by a computer, execute relevant calculations based on values obtained from analysis of one or more biological sample from an individual (e.g., gene expression levels, normalization, thresholding, and conversion of values from assays to a score and/or graphical depiction of likelihood of recurrence/response to chemotherapy, gene co-expression or clique analysis, and the like). The computer program product has stored therein a computer program for performing the calculation.

The present disclosure provides systems for executing the program described above, which system generally includes: a) a central computing environment; b) an input device, operatively connected to the computing environment, to receive patient data, wherein the patient data can include, for example, expression level or other value obtained from an assay using a biological sample from the patient, or microarray data, as described in detail above; c) an output device, connected to the computing environment, to provide information to a user (e.g., medical personnel); and d) an algorithm executed by the central computing environment (e.g., a processor), where the algorithm is executed based on the data received by the input device, and wherein the algorithm calculates a RS, risk or benefit group classification, gene co-expression analysis, thresholding, or other functions described herein. The methods provided by the present invention may also be automated in whole or in part.

All aspects of the present invention may also be practiced such that a limited number of additional genes that are co-expressed with the disclosed genes, for example as evidenced by statistically meaningful Pearson and/or Spearman correlation coefficients, are included in a prognostic test in addition to and/or in place of disclosed genes.

Having described the invention, the same will be more readily understood through reference to the following Examples, which are provided by way of illustration, and are not intended to limit the invention in any way.

EXAMPLES

Example 1: Selection of Genes for Algorithm Development

A gene identification study to identify genes associated with clinical recurrence is described in U.S. Provisional Application Nos. 61/294,038, filed Jan. 11, 2010, and 61/346,230, filed May 19, 2010, and in U.S. Application Publication No. 2011/0171633, filed Jan. 7, 2011, and published Jul. 14, 2011 (all of which are hereby incorporated by reference). Briefly, patients with stage I-III ccRCC who underwent nephrectomy at Cleveland Clinic between 1985 and 2003 with archived paraffin-embedded nephrectomy samples were identified. RNA was extracted from 6×10 μm dissected tumor sections and RNA expression quantified for 732 genes (including 5 reference genes) using RT-PCR. The primary endpoint was recurrence-free interval (RFI), defined as time from nephrectomy to first recurrence or death clue to RCC. 931 patients with complete clinical/pathology data and tissue blocks were evaluable. Patient characteristics were: 63% male, median age 61, stage I (68%), II (10%) and III (22%), median follow-up of 5.6 years, 5-year recurrence rates in stage I, II, and III were 10%, 29%, and 45% respectively. Clinical/pathology covariates significantly associated with RFI included microscopic necrosis, Fuhrman grade, stage, tumor size and lymph node involvement (all p<0.001).

Based on the results of the identification study, 448 genes were significantly (p<0.05, unadjusted; Cox models) associated with RFI. For the majority of these genes (366 (82%)), increased expression was associated with better outcome. Many of the genes were significantly (p<0.05) associated with necrosis (503 genes), Fuhrman grade (494), stage (482), tumor size (492), and nodal status (183). 300 genes were significantly (p<0.05, unadjusted) associated with at least 4 of the 5 pathologic and clinical covariates described above.

A smaller set of 72 genes was selected for developing multi-gene models as follows: 29 genes associated with RFI after adjustment for disease stage, Fuhrman grade, tumor size, necrosis and nodal status controlling false discovery rate (FDR) at 10%; the top 14 genes associated with RFI in univariate analyses; 12 genes that were members of the vascular endothelial growth factor/mammalian target of rapamycin (VEGF/mTOR) vascularization pathway; and 17 genes from additional biological pathways that were identified by principal component analysis (PCA). These data were used to select the final 11 cancer-related genes and 5 reference genes and to develop a multi-gene algorithm to predict recurrence of ccRCC for patients with stage I/II/III renal cancer.

Example 2: Algorithm Development

The genes identified in the studies described in Example 1 were considered for inclusion in the Recurrence Score. A smaller set of 72 genes was selected as follows:

29 genes associated with RFI after covariate adjustment and FDR control at 10% using Storey's procedure (Storey JD (2002) A direct approach to false discovery rates. *Journal of the Royal Statistical Society: Series B* 64:479-498; Storey J D, Taylor J E, Siegmund DO (2004) Strong control, conservative point estimation and simultaneous conservative consistency of false discovery rates: a unified approach. *Journal of the Royal Statistical Society, Series B* 66:187-205).

14 genes most significant before covariate adjustment
12 genes members of VEGF/mTOR pathways
17 genes were selected by principal component analysis to identify genes from additional pathways To determine the association between each of the 72 genes and RFI, univariate and multivariable analyses were used. Tables 1A (univariate analysis) and 1B (multivariable analysis) report the Hazard Ratio, 95% confidence interval, Chi-squared, p-value, and q-value for each of the 72 genes.

TABLE 1A

Univariate analysis for 72 genes: association with RFI

| Rank by HR | Official Symbol | N | HR | 95% CI | Chi-Sq | p-value | q-value |
|---|---|---|---|---|---|---|---|
| 22 | A2M | 931 | 0.56 | (0.50, 0.63) | 83.81 | <0.001 | <0.001 |
| 29 | ADD1 | 931 | 0.59 | (0.53, 0.65) | 80.56 | <0.001 | <0.001 |
| 58 | ANGPTL3 | 931 | 0.74 | (0.62, 0.89) | 13.23 | <0.001 | <0.001 |
| 26 | APOLD1 | 930 | 0.57 | (0.51, 0.64) | 78.75 | <0.001 | <0.001 |
| 4 | AQP1 | 931 | 0.50 | (0.45, 0.56) | 128.63 | <0.001 | <0.001 |
| 34 | BUB1* | 929 | 1.58 | (1.41, 1.76) | 55.55 | <0.001 | <0.001 |
| 24 | C13orf15 | 931 | 0.57 | (0.51, 0.63) | 86.84 | <0.001 | <0.001 |
| 40 | CA12* | 931 | 1.49 | (1.27, 1.73) | 26.27 | <0.001 | <0.001 |
| 42 | CASP10 | 930 | 0.69 | (0.61, 0.78) | 33.10 | <0.001 | <0.001 |
| 73 | CCL5 | 931 | 0.99 | (0.87, 1.13) | 0.02 | 0.894 | 0.455 |
| 48 | CCNB1* | 930 | 1.42 | (1.30, 1.55) | 42.47 | <0.001 | <0.001 |
| 66 | CCR7 | 931 | 0.86 | (0.75, 0.99) | 4.88 | 0.027 | 0.021 |
| 69 | CD8A | 931 | 0.92 | (0.80, 1.05) | 1.69 | 0.194 | 0.122 |
| 30 | CEACAM1 | 931 | 0.59 | (0.51, 0.67) | 62.18 | <0.001 | <0.001 |
| 27 | CX3CL1 | 929 | 0.58 | (0.52, 0.65) | 78.26 | <0.001 | <0.001 |
| 68 | CXCL10 | 931 | 0.89 | (0.78, 1.01) | 3.29 | 0.070 | 0.049 |
| 67 | CXCL9 | 931 | 0.87 | (0.76, 0.99) | 4.38 | 0.036 | 0.027 |
| 47 | CYR61 | 930 | 0.70 | (0.62, 0.80) | 27.32 | <0.001 | <0.001 |
| 23 | EDNRB | 931 | 0.56 | (0.50, 0.63) | 88.22 | <0.001 | <0.001 |
| 53 | EGR1 | 930 | 0.72 | (0.63, 0.82) | 24.84 | <0.001 | <0.001 |
| 1 | EMCN | 931 | 0.43 | (0.38, 0.49) | 159.51 | <0.001 | <0.001 |
| 56 | ENO2* | 930 | 1.38 | (1.19, 1.60) | 18.87 | <0.001 | <0.001 |
| 17 | EPAS1 | 930 | 0.55 | (0.49, 0.61) | 91.16 | <0.001 | <0.001 |
| 31 | FLT1 | 931 | 0.59 | (0.53, 0.66) | 79.86 | <0.001 | <0.001 |
| 14 | FLT4 | 929 | 0.54 | (0.47, 0.63) | 73.61 | <0.001 | <0.001 |
| 62 | HIF1AN | 931 | 0.77 | (0.68, 0.86) | 18.49 | <0.001 | <0.001 |
| 45 | HLA-DPB1 | 931 | 0.70 | (0.61, 0.79) | 29.36 | <0.001 | <0.001 |
| 35 | ICAM2 | 931 | 0.64 | (0.56, 0.73) | 44.18 | <0.001 | <0.001 |
| 19 | ID1 | 930 | 0.55 | (0.49, 0.62) | 88.60 | <0.001 | <0.001 |
| 50 | IL6* | 931 | 1.41 | (1.26, 1.58) | 31.01 | <0.001 | <0.001 |
| 36 | IL8* | 931 | 1.53 | (1.37, 1.71) | 48.21 | <0.001 | <0.001 |
| 65 | ITGB1 | 930 | 0.83 | (0.72, 0.96) | 6.93 | 0.008 | 0.007 |
| 72 | ITGB5 | 931 | 0.97 | (0.85, 1.11) | 0.22 | 0.640 | 0.341 |
| 20 | JAG1 | 929 | 0.55 | (0.49, 0.62) | 81.10 | <0.001 | <0.001 |
| 12 | KDR | 931 | 0.54 | (0.48, 0.60) | 99.81 | <0.001 | <0.001 |
| 54 | KIT | 931 | 0.72 | (0.61, 0.84) | 19.21 | <0.001 | <0.001 |
| 21 | KL | 931 | 0.55 | (0.49, 0.62) | 88.21 | <0.001 | <0.001 |
| 55 | KRAS | 931 | 0.72 | (0.64, 0.80) | 29.32 | <0.001 | <0.001 |
| 63 | LAMB1* | 931 | 1.25 | (1.09, 1.43) | 10.19 | 0.001 | 0.001 |
| 9 | LDB2 | 931 | 0.52 | (0.47, 0.59) | 106.34 | <0.001 | <0.001 |
| 52 | LMNB1* | 929 | 1.40 | (1.23, 1.60) | 24.87 | <0.001 | <0.001 |
| 49 | LOX* | 930 | 1.42 | (1.23, 1.63) | 24.39 | <0.001 | <0.001 |
| 43 | MAP2K3 | 930 | 0.69 | (0.60, 0.79) | 27.34 | <0.001 | <0.001 |
| 41 | MMP14* | 931 | 1.47 | (1.28, 1.70) | 29.17 | <0.001 | <0.001 |
| 60 | MTOR | 931 | 0.75 | (0.66, 0.85) | 18.25 | <0.001 | <0.001 |
| 18 | NOS3 | 931 | 0.55 | (0.48, 0.62) | 87.41 | <0.001 | <0.001 |
| 16 | NUDT6 | 929 | 0.54 | (0.47, 0.63) | 72.15 | <0.001 | <0.001 |
| 61 | PDGFA | 930 | 0.75 | (0.68, 0.83) | 24.73 | <0.001 | <0.001 |
| 33 | PDGFB | 930 | 0.63 | (0.57, 0.70) | 62.54 | <0.001 | <0.001 |
| 37 | PDGFC | 931 | 0.66 | (0.59, 0.74) | 43.48 | <0.001 | <0.001 |
| 28 | PDGFD | 931 | 0.58 | (0.52, 0.66) | 71.07 | <0.001 | <0.001 |
| 57 | PDGFRB | 931 | 0.73 | (0.65, 0.83) | 22.44 | <0.001 | <0.001 |
| 3 | PPAP2B | 931 | 0.50 | (0.45, 0.55) | 135.14 | <0.001 | <0.001 |
| 32 | PRKCH | 920 | 0.63 | (0.56, 0.69) | 62.51 | <0.001 | <0.001 |
| 6 | PTPRB | 930 | 0.51 | (0.46, 0.57) | 129.10 | <0.001 | <0.001 |
| 44 | PTTG1* | 931 | 1.45 | (1.27, 1.66) | 29.43 | <0.001 | <0.001 |
| 64 | RAF1 | 931 | 0.81 | (0.72, 0.91) | 11.34 | <0.001 | 0.001 |
| 10 | RGS5 | 928 | 0.52 | (0.47, 0.59) | 103.64 | <0.001 | <0.001 |
| 7 | SDPR | 931 | 0.52 | (0.45, 0.59) | 96.39 | <0.001 | <0.001 |
| 39 | SGK1 | 930 | 0.67 | (0.60, 0.75) | 40.73 | <0.001 | <0.001 |
| 11 | SHANK3 | 931 | 0.53 | (0.47, 0.59) | 103.99 | <0.001 | <0.001 |
| 15 | SNRK | 931 | 0.54 | (0.49, 0.60) | 107.74 | <0.001 | <0.001 |

TABLE 1A-continued

Univariate analysis for 72 genes: association with RFI

| | Official | | | Association with RFI | | | |
|---|---|---|---|---|---|---|---|
| Rank by HR | Symbol | N | HR | 95% CI | Chi-Sq | p-value | q-value |
| 46 | SPP1* | 928 | 1.43 | (1.25, 1.63) | 27.72 | <0.001 | <0.001 |
| 2 | TEK | 931 | 0.47 | (0.40, 0.54) | 106.55 | <0.001 | <0.001 |
| 13 | TGFBR2 | 930 | 0.54 | (0.48, 0.62) | 79.22 | <0.001 | <0.001 |
| 5 | TIMP3 | 931 | 0.50 | (0.44, 0.57) | 105.15 | <0.001 | <0.001 |
| 25 | TPX2* | 931 | 1.75 | (1.54, 1.99) | 71.81 | <0.001 | <0.001 |
| 8 | TSPAN7 | 930 | 0.52 | (0.47, 0.58) | 117.10 | <0.001 | <0.001 |
| 70 | TUBB2A* | 929 | 1.09 | (0.96, 1.24) | 1.64 | 0.200 | 0.125 |
| 51 | UGCG | 929 | 0.71 | (0.62, 0.82) | 23.04 | <0.001 | <0.001 |
| 38 | VCAM1 | 931 | 0.66 | (0.59, 0.75) | 41.89 | <0.001 | <0.001 |
| 59 | VEGFA | 931 | 0.75 | (0.67, 0.84) | 21.30 | <0.001 | <0.001 |

Key:
Significant Associations (p < 0.05)
Genes marked with an asterisk (*) are associated such that increased expression is associated with worse outcome
Genes in bold are the top 10 genes with respect to magnitude of the Hazard Ratio (HR)

TABLE 1B

Multivariable analysis for 72 genes: association with RFI

| | Official | | | Association with RFI Adjusted for 5 Clin/path Covariates | | | |
|---|---|---|---|---|---|---|---|
| Rank by HR | Symbol | N | HR | 95% CI | Chi-Sq | p-value | q-value |
| 22 | A2M | 928 | 0.93 | (0.80, 1.08) | 0.99 | 0.3191 | 0.5394 |
| 29 | ADD1 | 928 | 0.85 | (0.73, 0.98) | 4.50 | 0.0339 | 0.2249 |
| 58 | ANGPTL3 | 928 | 0.79 | (0.67, 0.94) | 8.53 | 0.0035 | 0.0907 |
| 26 | APOLD1 | 927 | 0.78 | (0.68, 0.91) | 10.07 | 0.0015 | 0.0793 |
| 4 | AQP1 | 928 | 0.79 | (0.69, 0.91) | 10.15 | 0.0014 | 0.0793 |
| 34 | BUB1* | 926 | 1.15 | (1.01, 1.31) | 4.52 | 0.0335 | 0.2249 |
| 24 | C13orf15 | 928 | 0.89 | (0.78, 1.03) | 2.42 | 0.1197 | 0.3674 |
| 40 | CA12* | 928 | 1.08 | (0.95, 1.23) | 1.46 | 0.2267 | 0.4919 |
| 42 | CASP10 | 927 | 0.82 | (0.73, 0.93) | 9.25 | 0.0024 | 0.0793 |
| 73 | CCL5 | 928 | 0.78 | (0.68, 0.89) | 12.98 | 0.0003 | 0.0529 |
| 48 | CCNB1* | 927 | 1.14 | (1.02, 1.28) | 4.73 | 0.0296 | 0.2249 |
| 66 | CCR7 | 928 | 0.80 | (0.69, 0.92) | 9.58 | 0.0020 | 0.0793 |
| 69 | CD8A | 928 | 0.83 | (0.73, 0.95) | 7.60 | 0.0058 | 0.1154 |
| 30 | CEACAM1 | 928 | 0.81 | (0.70, 0.93) | 9.37 | 0.0022 | 0.0793 |
| 27 | CX3CL1 | 926 | 0.81 | (0.71, 0.92) | 9.44 | 0.0021 | 0.0793 |
| 68 | CXCL10 | 928 | 0.86 | (0.75, 0.99) | 4.58 | 0.0323 | 0.2249 |
| 67 | CXCL9 | 928 | 0.80 | (0.70, 0.91) | 11.74 | 0.0006 | 0.0772 |
| 47 | CYR61 | 927 | 0.93 | (0.81, 1.08) | 0.84 | 0.3603 | 0.5581 |
| 23 | EDNRB | 928 | 0.86 | (0.74, 0.99) | 4.22 | 0.0400 | 0.2411 |
| 53 | EGR1 | 927 | 0.91 | (0.79, 1.04) | 1.93 | 0.1652 | 0.4234 |
| 1 | EMCN | 928 | 0.68 | (0.57, 0.80) | 19.87 | <0.001 | 0.0042 |
| 56 | ENO2* | 927 | 1.17 | (1.02, 1.34) | 4.81 | 0.0284 | 0.1899 |
| 17 | EPAS1 | 927 | 0.84 | (0.72, 0.99) | 4.17 | 0.0411 | 0.2411 |
| 31 | FLT1 | 928 | 0.91 | (0.80, 1.05) | 1.57 | 0.2106 | 0.4919 |
| 14 | FLT4 | 926 | 0.86 | (0.73, 1.02) | 3.11 | 0.0776 | 0.3289 |
| 62 | HIF1AN | 928 | 1.02 | (0.90, 1.16) | 0.10 | 0.7571 | 0.7052 |
| 45 | HLA-DPB1 | 928 | 0.82 | (0.71, 0.93) | 8.48 | 0.0036 | 0.0907 |
| 35 | ICAM2 | 928 | 0.83 | (0.72, 0.95) | 6.80 | 0.0091 | 0.1407 |
| 19 | ID1 | 927 | 0.83 | (0.71, 0.96) | 5.87 | 0.0154 | 0.1899 |
| 50 | IL6* | 928 | 1.04 | (0.92, 1.18) | 0.46 | 0.4994 | 0.6384 |
| 36 | IL8* | 928 | 1.11 | (0.98, 1.26) | 2.89 | 0.0890 | 0.3350 |
| 65 | ITGB1 | 927 | 1.16 | (1.01, 1.33) | 4.21 | 0.0402 | 0.2411 |
| 72 | ITGB5 | 928 | 1.25 | (1.09, 1.43) | 9.92 | 0.0016 | 0.0793 |
| 20 | JAG1 | 926 | 0.88 | (0.75, 1.03) | 2.56 | 0.1097 | 0.3644 |
| 12 | KDR | 928 | 0.86 | (0.74, 1.00) | 3.71 | 0.0541 | 0.2818 |
| 54 | KIT | 928 | 0.97 | (0.83, 1.13) | 0.19 | 0.6591 | 0.6861 |
| 21 | KL | 928 | 0.86 | (0.75, 0.98) | 5.16 | 0.0231 | 0.2238 |
| 55 | KRAS | 928 | 0.89 | (0.78, 1.03) | 2.30 | 0.1294 | 0.3757 |
| 63 | LAMB1* | 928 | 1.20 | (1.05, 1.38) | 7.35 | 0.0067 | 0.0793 |
| 9 | LDB2 | 928 | 0.82 | (0.71, 0.95) | 6.78 | 0.0092 | 0.1407 |
| 52 | LMNB1* | 926 | 1.02 | (0.89, 1.16) | 0.05 | 0.8287 | 0.7269 |
| 49 | LOX* | 927 | 0.98 | (0.86, 1.12) | 0.08 | 0.7751 | 0.7115 |
| 43 | MAP2K3 | 927 | 0.92 | (0.79, 1.06) | 1.32 | 0.2508 | 0.5018 |
| 41 | MMP14* | 928 | 1.16 | (1.02, 1.33) | 4.90 | 0.0269 | 0.2249 |
| 60 | MTOR | 928 | 0.93 | (0.81, 1.07) | 0.92 | 0.3371 | 0.5441 |
| 18 | NOS3 | 928 | 0.78 | (0.68, 0.90) | 11.32 | 0.0008 | 0.0774 |
| 16 | NUDT6 | 926 | 0.77 | (0.66, 0.90) | 10.77 | 0.0010 | 0.0793 |
| 61 | PDGFA | 927 | 0.97 | (0.85, 1.12) | 0.16 | 0.6910 | 0.6914 |

TABLE 1B-continued

Multivariable analysis for 72 genes: association with RFI

| Rank by HR | Official Symbol | N | HR | 95% CI | Chi-Sq | p-value | q-value |
|---|---|---|---|---|---|---|---|
| 33 | PDGFB | 927 | 0.94 | (0.81, 1.08) | 0.84 | 0.3595 | 0.5581 |
| 37 | PDGFC | 928 | 0.93 | (0.82, 1.06) | 1.18 | 0.2773 | 0.5283 |
| 28 | PDGFD | 928 | 0.91 | (0.79, 1.05) | 1.54 | 0.2151 | 0.4919 |
| 57 | PDGFRB | 928 | 1.03 | (0.90, 1.18) | 0.16 | 0.6882 | 0.6914 |
| 3 | PPAP2B | 928 | 0.74 | (0.65, 0.85) | 16.15 | 0.0001 | 0.0148 |
| 32 | PRKCH | 917 | 0.82 | (0.72, 0.93) | 9.36 | 0.0022 | 0.0793 |
| 6 | PTPRB | 927 | 0.80 | (0.69, 0.92) | 8.83 | 0.0030 | 0.0877 |
| 44 | PTTG1* | 928 | 1.01 | (0.88, 1.16) | 0.03 | 0.8727 | 0.7688 |
| 64 | RAF1 | 928 | 1.06 | (0.92, 1.22) | 0.68 | 0.4086 | 0.5875 |
| 10 | RGS5 | 925 | 0.85 | (0.73, 1.00) | 3.91 | 0.0480 | 0.2661 |
| 7 | SDPR | 928 | 0.80 | (0.69, 0.93) | 8.08 | 0.0045 | 0.1037 |
| 39 | SGK1 | 927 | 0.83 | (0.72, 0.95) | 6.64 | 0.0100 | 0.1437 |
| 11 | SHANK3 | 928 | 0.84 | (0.71, 0.98) | 4.65 | 0.0311 | 0.2249 |
| 15 | SNRK | 928 | 0.81 | (0.71, 0.92) | 9.09 | 0.0026 | 0.0809 |
| 46 | SPP1* | 925 | 1.17 | (1.03, 1.33) | 6.11 | 0.0134 | 0.2238 |
| 2 | TEK | 928 | 0.78 | (0.65, 0.93) | 7.58 | 0.0059 | 0.1154 |
| 13 | TGFBR2 | 927 | 0.85 | (0.73, 0.99) | 4.48 | 0.0343 | 0.2249 |
| 5 | TIMP3 | 928 | 0.83 | (0.70, 0.97) | 5.75 | 0.0165 | 0.1960 |
| 25 | TPX2* | 928 | 1.19 | (1.05, 1.36) | 7.29 | 0.0069 | 0.1258 |
| 8 | TSPAN7 | 927 | 0.83 | (0.71, 0.95) | 6.65 | 0.0099 | 0.1437 |
| 70 | TUBB2A* | 926 | 1.21 | (1.06, 1.39) | 8.04 | 0.0046 | 0.0877 |
| 51 | UGCG | 926 | 0.91 | (0.80, 1.04) | 1.98 | 0.1592 | 0.4100 |
| 38 | VCAM1 | 928 | 0.92 | (0.81, 1.04) | 1.88 | 0.1708 | 0.4271 |
| 59 | VEGFA | 928 | 1.01 | (0.88, 1.17) | 0.03 | 0.8727 | 0.7408 |

Key:
Significant Associations (p < 0.05)
Genes marked with an asterisk (*) are associated such that increased expression is associated with worse outcome
Genes in bold are the top 10 genes w.r.t. magnitude of the Hazard Ratio (HR)
Analysis in this table is adjusted for stage, necrosis status, tumor size, Furhman grade, nodal status.

The 72-gene set was reduced further to 14 genes by exploring the contribution of genes to the multi-gene models, consistency of performance across endpoints, and analytical performance. Selection of the final set of 11 genes was based on multivariable analyses which considered all possible combinations of the 14 genes and ranked models by standardized hazard ratio for the multi-gene score (Crager, Journal of Applied Statistics 2012 February; 36(2), 399-417) corrected for regression to the mean (RM). This method corrects for selecting among combinations of genes and considers combinations selected from all 732 genes investigated in the gene identification study. The identified maximum RM-corrected hazard ratio is unbiased (Crager, Stat Med. 2010 Jan. 15; 29(1):33-45.)) and provides a realistic estimate of the performance of the given multi-gene model on an independent dataset.

Additional considerations for gene selection included assay performance of individual genes (heterogeneity) when assessed in fixed paraffin-embedded tumor tissue, level and variability of gene expression, and functional form of the relationship with clinical outcome.

The gene expression panel included cancer-related genes and reference genes, as shown in Table 2.

TABLE 2

| Gene Expression Panel | | | |
|---|---|---|---|
| Cancer-related Genes | Accession Number | Reference Genes | Accession Number |
| APOLD1 | NM_030817 | AAMP | NM_001087 |
| CCL5 | NM_002985 | ARF1 | NM_001658 |
| CEACAM1 | NM_001712 | ATP5E | NM_006886 |

TABLE 2-continued

| Gene Expression Panel | | | |
|---|---|---|---|
| Cancer-related Genes | Accession Number | Reference Genes | Accession Number |
| CX3CL1 | NM_002996 | GPX1 | NM_000581 |
| EDNRB | NM_000115 | RPLP1 | NM_213725 |
| EIF4EBP1 | NM_004095 | | |
| IL6 | NM_000600 | | |
| LMNB1 | NM_005573 | | |
| NOS3 | NM_000603 | | |
| PPAP2B | NM_003713 | | |
| TUBB2A | NM_001069 | | |

Overview of the Algorithm for Obtaining a Recurrence Score

After using quantitative RT-PCR to determine the mRNA expression levels of the chosen genes, the genes were grouped into subsets. Genes known to be associated with vascular and/or angiogenesis functions were grouped in a "vascular normalization" gene group. Genes known to be associated with immune function were grouped in an "immune response" gene group. Genes associated with key cell growth and cell division pathway(s) were grouped in a "cell growth/division" gene group.

The gene expression for some genes may be thresholded if the relationship between the term and the risk of recurrence is non-linear or expression of the gene is relatively low. For example, when the expression of IL6 is found at <4 $C_T$ the value is fixed at 4 $C_T$.

In the next step, the measured tumor level of each mRNA in a subset was multiplied by a coefficient reflecting its relative intra-set contribution to the risk of cancer recurrence. This product was added to the other products between mRNA levels in the subset and their coefficients, to yield a term, e.g. a vascular normalization term, a cell growth/division term, and an immune response term. For example, the immune response term is (0.5 CCL5+CEACAM1+CX3CL1)/3 (see the Example below).

The contribution of each term to the overall recurrence score was then weighted by use of a coefficient. For example, the immune response term was multiplied by −0.31.

The sum of the terms obtained provided the recurrence score (RS).

A relationship between recurrence score (RS) and risk of recurrence has been found by measuring expression of the test and reference genes in biopsied tumor specimens from a population of patients with clear cell renal cell carcinoma and applying the algorithm.

The RS scale generated by the algorithm of the present invention can be adjusted in various ways. Thus, while the RS scale specifically described above effectively runs from −3.2 to −0.2, the range could be selected such that the scale run from 0 to 10, 0 to 50, or 0 to 100, for example. For example, in a particular scaling approach, scaled recurrence score (RS) is calculated on a scale of 0 to 100. For convenience, 10 $C_T$ units are added to each measured $C_T$ value, and unscaled RS is calculated as described before. Scaled recurrence score values are calculated using the equations shown below.

The Recurrence Score (RS) on a scale from 0 to 100 was derived from the reference-normalized expression measurements as follows:

RSu=−0.45×Vascular Normalization Gene Group Score−0.31×Immune Response Gene Group Score+0.27×Cell Growth/Division Gene Group Score+0.04×IL6

The RSu (Recurrence Score unsealed) is then rescaled to be between 0 and 100:

RS=(RSu+3.7)×26.4,

If (RSu+3.7)×26.4<0, then RS=0.

If (RSu+3.7)×26.4>100, then RS=100.

Example 3: Performance of the Algorithm

The performance of the final genes included in the algorithm with and without adjustment for correction for regression to the mean with respect to the endpoint of recurrence is summarized in Table 3.

When using analyses that control the false discovery rate such as Storey's procedure, increasing the proportion of genes with little or no association decreases the identification power even for genes strongly associated with outcome. Therefore, analyzing all of the genes together as one very large set can be expected to produce an analysis with lower power to identify truly associated genes. To mitigate this issue, a "separate class" analysis (Efron B. Simultaneous inference: When should hypothesis testing problems be combined. *Ann. Appl. Statist.* 2008; 2:197-223.) was done. In the separate class analysis, false discovery rates are calculated within each gene class, using information from all the genes to improve the accuracy of the calculation. Two gene classes were selected prospectively on the basis of prior information and/or belief about their association with cancer recurrence, and the remaining genes places in the third class.

TABLE 3

Performance of the Genes in the Algorithm

| N | Class | Official Symbol | Higher expression more (+)/ less (−) risk | ASHR | SHR | (95% CI) | p-value | q-Value (FDR) | MLB ASHR | RM-Corrected ASHR |
|---|---|---|---|---|---|---|---|---|---|---|
| 1 | 2 | PPAP2B | (−) | 2.00 | 0.50 | (0.45, 0.55) | <0.001 | <0.001 | 1.73 | 1.97 |
| 2 | 1 | NOS3 | (−) | 1.83 | 0.55 | (0.48, 0.62) | <0.001 | <0.001 | 1.59 | 1.80 |
| 3 | 2 | EDNRB | (−) | 1.78 | 0.56 | (0.50, 0.63) | <0.001 | <0.001 | 1.58 | 1.76 |
| 4 | 2 | APOLD1 | (−) | 1.74 | 0.57 | (0.51, 0.64) | <0.001 | <0.001 | 1.55 | 1.72 |
| 5 | 3 | CX3CL1 | (−) | 1.72 | 0.58 | (0.52, 0.65) | <0.001 | <0.001 | 1.45 | 1.68 |
| 6 | 3 | CEACAM1 | (−) | 1.70 | 0.59 | (0.51, 0.67) | <0.001 | <0.001 | 1.42 | 1.64 |
| 7 | 3 | IL6* | (+) | 1.38 | 1.38 | (1.25, 1.53) | <0.001 | <0.001 | 1.24 | 1.35 |
| 8 | 3 | LMNB1 | (+) | 1.40 | 1.40 | (1.23, 1.60) | <0.001 | <0.001 | 1.22 | 1.34 |
| 9 | 3 | EIF4EBP1 | (+) | 1.19 | 1.19 | (1.04, 1.37) | 0.010 | 0.004 | 1.09 | 1.16 |
| 10 | 3 | TUBB2A | (+) | 1.09 | 1.09 | (0.96, 1.24) | 0.200 | 0.054 | 1.03 | 1.07 |
| 11 | 1 | CCL5 | (−) | 1.01 | 0.99 | (0.87, 1.13) | 0.894 | 0.125 | 1.01 | 1.03 |

Abbreviations:
ASHR = absolute standardized hazard ratio, RM = regression to the mean corrected, FDR = false discovery rate.
*IL6 expression thresholded at 4 CT.

where

Vascular Normalization Gene Group Score=(0.5 APOLD1+0.5 EDNRB+NOS3+PPA2B)/4

Cell Growth/Division Gene Group Score= (EIF4EBP1+1.3 LMNB1+TUBB2A)/3

Immune Response Gene Group Score=(0.5 CCL5+CEACAM1+CX3CL1)/3

In the Cox model stratified by stage, the final Recurrence Score yielded absolute standardized HR=2.16 (95% CI 1.89, 2.48) and regression to the mean corrected absolute standardized HR=1.91 (95% CI 1.38, 2.30) for the association with recurrence.

Performance of the Recurrence Score can also be demonstrated by the predictiveness curves (Hung Y, Pepe M S, Feng Z. (2007). Evaluating the predictiveness of a continuous marker. Biometrics 63:1181-1188.) shown in FIGS. 1A and 1B. These curves are plots of the estimated risk of recurrence (vertical axis) against the population quantile (rank) of the risk. The curve as a whole shows the population distribution of risk. More effective prognostic scores separate lower risk patients from higher risk patients, which are reflected by the curve separating from the average risk line. Risk cut-points can then be applied to describe how many patients fall into various risk groups. For example, the cut-points can be used to describe how many patients with stage 1 RCC have a risk>16%.

Example 4: Heterogeneity Study

An internal study examining the variability due to tissue heterogeneity was run on a sample of renal cancer fixed paraffin-embedded tissue (FPET) blocks. Eight (8) patients with two (2) blocks for each patient and three (3) sections within each block were assessed using the methods and algorithm provided in the above Examples. Heterogeneity was measured by assessing between block variability and within block variability. The between block variability measures the biological variability between FPET blocks within the same patient. This provides an estimate of the population level variability. The within block variability captures both the tissue heterogeneity within a block as well as the technical assay-related variability. The normalized individual gene scores as well as the Recurrence Score were calculated and within block, between block and between patient variability estimates were generated. The results of the analysis are listed in tables 4 and 5 below. The high ratio of the between patient variability to the between and within block variability is generally favorable. This indicates that the tissue heterogeneity and technical assay related variability is low compared with the clinically informative patient to patient variability in the individual gene measurements and the Recurrence Score.

TABLE 4

Recurrence Score Variance Component Estimates

| Variance Component | SD | Lower 95% | Upper 95% |
|---|---|---|---|
| Between Patient | 15.60 | 10.15 | 33.32 |
| Between Block | 4.74 | 3.16 | 9.45 |
| Within Block | 1.73 | 1.39 | 2.29 |

TABLE 5

Individual Normalized Gene Variance Component Estimates

| Gene | Variance Comp | SD | Lower 95% | Upper 95% |
|---|---|---|---|---|
| AAMP.1 | Between Patient | 0.39 | 0.26 | 0.84 |
| AAMP.1 | Between Block | 0.11 | 0.07 | 0.24 |
| AAMP.1 | Within Block | 0.06 | 0.05 | 0.08 |
| APOLD1.1 | Between Patient | 1.64 | 1.07 | 3.43 |
| APOLD1.1 | Between Block | 0.39 | 0.26 | 0.76 |
| APOLD1.1 | Within Block | 0.11 | 0.09 | 0.15 |
| ARF1.1 | Between Patient | 0.20 | 0.13 | 0.47 |
| ARF1.1 | Between Block | 0.10 | 0.07 | 0.21 |
| ARF1.1 | Within Block | 0.05 | 0.04 | 0.07 |
| ATP5E.1 | Between Patient | 0.19 | 0.12 | 0.42 |
| ATP5E.1 | Between Block | 0.08 | 0.05 | 0.17 |
| ATP5E.1 | Within Block | 0.04 | 0.03 | 0.06 |
| CCL5.2 | Between Patient | 0.72 | 0.46 | 1.57 |
| CCL5.2 | Between Block | 0.26 | 0.17 | 0.53 |
| CCL5.2 | Within Block | 0.12 | 0.10 | 0.16 |
| CEACAM1.1 | Between Patient | 0.58 | 0.34 | 1.87 |
| CEACAM1.1 | Between Block | 0.49 | 0.33 | 0.97 |
| CEACAM1.1 | Within Block | 0.17 | 0.14 | 0.23 |

TABLE 5-continued

Individual Normalized Gene Variance Component Estimates

| Gene | Variance Comp | SD | Lower 95% | Upper 95% |
|---|---|---|---|---|
| CX3CL1.1 | Between Patient | 1.36 | 0.89 | 2.84 |
| CX3CL1.1 | Between Block | 0.31 | 0.20 | 0.65 |
| CX3CL1.1 | Within Block | 0.18 | 0.14 | 0.23 |
| EDNRB.1 | Between Patient | 1.25 | 0.82 | 2.66 |
| EDNRB.1 | Between Block | 0.36 | 0.23 | 0.75 |
| EDNRB.1 | Within Block | 0.20 | 0.16 | 0.27 |
| EIF4EBP1.1 | Between Patient | 0.57 | 0.36 | 1.30 |
| EIF4EBP1.1 | Between Block | 0.25 | 0.17 | 0.52 |
| EIF4EBP1.1 | Within Block | 0.12 | 0.10 | 0.16 |
| GPX1.2 | Between Patient | 0.43 | 0.28 | 0.88 |
| GPX1.2 | Between Block | 0.04 | 0.02 | 0.12 |
| GPX1.2 | Within Block | 0.04 | 0.04 | 0.06 |
| IL6.3 | Between Patient | 1.24 | 0.81 | 2.60 |
| IL6.3 | Between Block | 0.28 | 0.18 | 0.62 |
| IL6.3 | Within Block | 0.19 | 0.15 | 0.25 |
| LMNB1.1 | Between Patient | 0.58 | 0.37 | 1.24 |
| LMNB1.1 | Between Block | 0.18 | 0.11 | 0.41 |
| LMNB1.1 | Within Block | 0.14 | 0.11 | 0.18 |
| NOS3.1 | Between Patient | 0.75 | 0.48 | 1.69 |
| NOS3.1 | Between Block | 0.32 | 0.21 | 0.70 |
| NOS3.1 | Within Block | 0.21 | 0.17 | 0.28 |
| PPAP2B.1 | Between Patient | 0.89 | 0.58 | 1.90 |
| PPAP2B.1 | Between Block | 0.28 | 0.19 | 0.56 |
| PPAP2B.1 | Within Block | 0.10 | 0.08 | 0.13 |
| RPLP1.1 | Between Patient | 0.38 | 0.24 | 0.82 |
| RPLP1.1 | Between Block | 0.13 | 0.09 | 0.27 |
| RPLP1.1 | Within Block | 0.05 | 0.04 | 0.07 |
| TUBB.1 | Between Patient | 0.52 | 0.34 | 1.07 |
| TUBB.1 | Between Block | 0.00 | . | . |
| TUBB.1 | Within Block | 0.15 | 0.12 | 0.19 |

Example 5: Additional Multi-Gene Combinations

A number of alternative multi-gene models were also evaluated, using either the dataset from the gene identification study or the dataset from the validation study. Additional representative gene combinations tested on the dataset from the gene identification study are shown in Table 6. Additional representative gene combinations tested on the dataset from the validation study are shown in Table 7. Models 1-4 shown in Table 6 were not tested on the dataset from the validation study, and so are omitted from Table 7. Those Tables both list calculated coefficients reflecting each gene's relative weight in an algorithm to predict the risk of cancer recurrence. The measured tumor level of each mRNA encoding the specific genes used in the various models tested (e.g., model 11 included APOLD1, NOS3, PPAP2B, and CEACAM1) was multiplied by the listed coefficient to produce an alternative score. The performance of each alternative score, as measured by absolute standard hazard ratios and the corresponding 95% confidence intervals, is also shown in the Tables. Where two genes are listed in the header row (e.g., APOLD1-EDNRB, IL6-IL8), that column lists the coefficient of the average measured tumor level of the mRNA encoding those two genes.

TABLE 6

Additional Gene Combinations Tested on the Gene ID Study Cohort

| Model | Abs Std HR | 95% CI | APOLD1 | EDNRB | APOLD_EDNRB | NOS3 | PPAP2B |
|---|---|---|---|---|---|---|---|
| 1 | 2.39 | (1.96-2.92) | 0.10065 | | | −0.14167 | |
| 2 | 2.41 | (1.95-3.17) | 0.04032 | | | −0.17261 | |
| 3 | 1.98 | (1.72-2.47) | | | | | |
| 4 | 1.65 | (1.45-2.03) | | | | | |
| 5 | 1.93 | (1.7-2.31) | | | −0.40375 | −0.35004 | |
| 6 | 2.04 | (1.81-2.51) | | | −0.17043 | | −0.58611 |
| 7 | 2.16 | (1.8-2.65) | −0.03371 | | | −0.28074 | −0.54832 |
| 8 | 2.15 | (1.81-2.68) | | −0.01887 | | −0.28464 | −0.54932 |
| 9 | 1.89 | (1.67-2.28) | −0.31267 | | | −0.40634 | |
| 10 | 2.15 | (1.81-2.61) | | | | −0.28998 | −0.56046 |
| 11 | 2.31 | (1.82-2.81) | −0.03748 | | | −0.26068 | −0.47770 |
| 12 | 2.27 | (1.85-2.75) | 0.08036 | | | −0.31162 | −0.47573 |
| 13 | 2.25 | (1.84-2.63) | −0.12126 | | | −0.37375 | |
| 14 | 2.27 | (1.82-2.78) | −0.07085 | | | | −0.49284 |
| 15 | 2.39 | (1.86-2.84) | | | | −0.26588 | −0.40334 |
| 16 | 2.31 | (1.91-2.83) | −0.15185 | | | −0.36766 | |
| 17 | 2.43 | (1.88-3.05) | | | | −0.28260 | −0.38388 |
| 18 | 2.38 | (1.8-2.85) | −0.06826 | | | −0.43101 | |
| 19 | 2.42 | (1.83-2.94) | | | | −0.30592 | −0.34043 |
| 20 | 2.26 | (1.79-2.66) | −0.10715 | | | −0.38255 | |
| 21 | 2.39 | (1.84-2.89) | | | | −0.26687 | −0.40513 |

| Model | CCL5 | CEACAM1 | CX3CL1 | EIF4EBP1 | LMNB1 | TUBB2A | IL6_IL8 | EMCN |
|---|---|---|---|---|---|---|---|---|
| 1 | | | | | | | | −0.85086 |
| 2 | | | | | | | 0.28445 | −0.70622 |
| 3 | | −0.32605 | −0.37949 | | | | 0.22783 | |
| 4 | | | | 0.07930 | 0.25017 | | 0.44323 | |
| 5 | | | | | | | | |
| 6 | | | | | | | | |
| 7 | | | | | | | | |
| 8 | | | | | | | | |
| 9 | | | | | | | | |
| 10 | | | | | | | | |
| 11 | | −0.26609 | | | | | | |
| 12 | | | −0.28130 | | | | | |
| 13 | | −0.29197 | −0.31655 | | | | | |
| 14 | | −0.24382 | −0.21409 | | | | | |
| 15 | | −0.22926 | −0.23534 | | | | | |
| 16 | | −0.28550 | −0.31272 | 0.23230 | | | | |
| 17 | | −0.22316 | −0.24918 | 0.20891 | | | | |
| 18 | | −0.27172 | −0.31025 | | 0.22880 | | | |
| 19 | | −0.22674 | −0.24106 | | 0.13465 | | | |
| 20 | | −0.31643 | −0.30215 | | | 0.12387 | | |
| 21 | | −0.25692 | −0.21438 | | | 0.15545 | | |

TABLE 7

Additional Gene Combinations Tested on the Validation Study Cohort

| Model | Abs Std HR | 95% CI | APOLD1 | EDNRB | APOLD_EDNRB | NOS3 | PPAP2B |
|---|---|---|---|---|---|---|---|
| 5 | 2.38 | (1.87-3.39) | | | −0.37408 | −0.49104 | |
| 6 | 2.26 | (1.84-3.09) | | | −0.37011 | | −0.47140 |
| 7 | 2.46 | (1.79-3.63) | −0.15921 | | | −0.44723 | −0.42667 |
| 8 | 2.49 | (1.77-3.57) | | −0.08781 | | −0.50150 | −0.47573 |
| 9 | 2.37 | (1.85-3.39) | −0.33393 | | | −0.53113 | |
| 10 | 2.50 | (1.78-3.37) | | | | −0.55049 | −0.54768 |
| 11 | 2.56 | (1.82-3.71) | −0.15909 | | | −0.43887 | −0.27880 |
| 12 | 2.46 | (1.75-3.81) | −0.08939 | | | −0.49354 | −0.28528 |
| 13 | 2.48 | (1.79-3.71) | −0.16355 | | | −0.49705 | |
| 14 | 2.35 | (1.78-3.52) | −0.30362 | | | | −0.27814 |
| 15 | 2.54 | (1.75-3.68) | | | | −0.54367 | −0.25241 |
| 16 | 2.52 | (1.87-4.36) | −0.27717 | | | −0.40990 | |
| 17 | 2.59 | (1.81-4.15) | | | | −0.52013 | −0.35305 |
| 18 | 2.64 | (1.8-4.2) | −0.16411 | | | −0.55241 | |
| 19 | 2.64 | (1.79-4.06) | | | | −0.67348 | −0.08793 |
| 20 | 2.62 | (1.81-3.87) | −0.21785 | | | −0.41881 | |
| 21 | 2.64 | (1.77-3.97) | | | | −0.52572 | −0.21665 |

TABLE 7-continued

Additional Gene Combinations Tested on the Validation Study Cohort

| Model | CCL5 | CEACAM1 | CX3CL1 | EIF4EBP1 | LMNB1 | TUBB2A | IL6 |
|---|---|---|---|---|---|---|---|
| 5 | | | | | | | |
| 6 | | | | | | | |
| 7 | | | | | | | |
| 8 | | | | | | | |
| 9 | | | | | | | |
| 10 | | | | | | | |
| 11 | | −0.26830 | | | | | |
| 12 | | | −0.29497 | | | | |
| 13 | | −0.25202 | −0.27392 | | | | |
| 14 | | −0.24210 | −0.21378 | | | | |
| 15 | | −0.21404 | −0.26516 | | | | |
| 16 | | −0.16163 | −0.22052 | 0.43141 | | | |
| 17 | | −0.11777 | −0.21773 | 0.42513 | | | |
| 18 | | −0.23417 | −0.17618 | | 0.46192 | | |
| 19 | | −0.22019 | −0.21252 | | 0.44420 | | |
| 20 | | −0.22971 | −0.29734 | | | −0.29777 | |
| 21 | | −0.20566 | −0.31766 | | | −0.25556 | |

What is claimed is:

1. A method for obtaining a quantitative score for a patient with kidney cancer, comprising:
measuring a level of RNA transcripts in a tumor sample obtained from the patient from a set of genes, the set of genes consisting of: APOLD1, EDNRB, NOS3, PPAP2B, EIF4EBP1, LMNB1, TUBB2A, CCL5, CEACAM1, CX3CL1, and IL-6 and at least one reference gene;
normalizing the level of the RNA transcripts of APOLD1, EDNRB, NOS3, PPAP2B, EIF4EBP1, LMNB1, TUBB2A, CCL5, CEACAM1, CX3CL1, and IL-6 against a level of the RNA transcript of the at least one reference gene to provide a normalized level of the RNA transcripts of APOLD1, EDNRB, NOS3, PPAP2B, EIF4EBP1, LMNB1, TUBB2A, CCL5, CEACAM1, CX3CL1, and IL-6; and
calculating a quantitative score result based on the normalized RNA transcript levels of CCL5, CEACAM1, and CXCL3, wherein the quantitative score is calculated as: (0.5CCL5+CEACAM1+CX3CL1)/3, where the gene name represents the normalized RNA transcript level of the named gene.

2. The method of claim 1, wherein the kidney cancer is renal cell carcinoma (RCC).

3. The method of claim 1, wherein the kidney cancer is clear cell renal cell carcinoma (ccRCC).

4. The method of claim 1, wherein the tumor sample is obtained from a biopsy.

5. The method of claim 1, wherein the tumor sample is paraffin-embedded and fixed.

6. The method of claim 1, further comprising generating a report comprising the quantitative score.

7. The method of claim 1, further comprising predicting a likelihood of recurrence of kidney cancer based on the quantitative score, wherein the quantitative score negatively correlates with risk of recurrence of kidney cancer.

8. The method of claim 1, further comprising classifying the patient's risk of recurrence of kidney cancer based on the quantitative score by comparing the quantitative score to a quantitative score associated with average risk of recurrence for kidney cancer patients.

9. The method of claim 8, wherein an increase in the quantitative score correlates with reduced risk of recurrence.

10. A method for obtaining a quantitative score for a patient with kidney cancer, comprising:
measuring a level of RNA transcripts in a tumor sample obtained from the patient from a set of up to 11 genes, the set of genes comprising CCL5, CEACAM1, and CX3CL1 and at least one reference gene;
normalizing the level of the RNA transcripts of CCL5, CEACAM1, and CX3CL1 against a level of the RNA transcript of the at least one reference gene to provide a normalized level of the RNA transcripts of CCL5, CEACAM1, and CX3CL1; and
calculating a quantitative score result based on the normalized RNA transcript levels of CCL5, CEACAM1, and CXCL3, wherein the quantitative score is calculated as: (0.5CCL5+CEACAM1+CX3CL1)/3, where the gene name represents the normalized RNA transcript level of the named gene.

11. The method of claim 10, wherein the kidney cancer is renal cell carcinoma (RCC).

12. The method of claim 10, wherein the kidney cancer is clear cell renal cell carcinoma (ccRCC).

13. The method of claim 10, wherein the tumor sample is obtained from a biopsy.

14. The method of claim 10, wherein the tumor sample is paraffin-embedded and fixed.

15. The method of claim 10, further comprising generating a report comprising the quantitative score.

16. The method of claim 10, wherein the set of up to 11 genes further comprises at least one of APOLD1, EDNRB, NOS3, PPAP2B, EIF4EBP1, LMNB1, TUBB2A, and IL-6.

17. The method of claim 10, further comprising predicting a likelihood of recurrence of kidney cancer based on the quantitative score, wherein the quantitative score negatively correlates with risk of recurrence of kidney cancer.

18. The method of claim 10, further comprising classifying the patient's risk of recurrence of kidney cancer based on the quantitative score by comparing the quantitative score to a quantitative score associated with average risk of recurrence for kidney cancer patients.

19. The method of claim 18, wherein an increase in the quantitative score correlates with reduced risk of recurrence.

* * * * *